(12) United States Patent
Detweiler et al.

(10) Patent No.: US 11,364,061 B2
(45) Date of Patent: Jun. 21, 2022

(54) IMPLANT POSITIONING DEVICES AND METHODS

(71) Applicant: JACE MEDICAL, LLC, Winona Lake, IN (US)

(72) Inventors: Jason F. Detweiler, Warsaw, IN (US); Scott Steffensmeier, Winona Lake, IN (US)

(73) Assignee: Jace Medical, LLC, Warsaw, IN (US)

( * ) Notice: Subject to any disclaimer, the term of this patent is extended or adjusted under 35 U.S.C. 154(b) by 230 days.

(21) Appl. No.: 16/142,540

(22) Filed: Sep. 26, 2018

(65) Prior Publication Data

US 2019/0090925 A1 Mar. 28, 2019

Related U.S. Application Data

(60) Provisional application No. 62/564,037, filed on Sep. 27, 2017.

(51) Int. Cl.
| | |
|---|---|
| *A61F 2/46* | (2006.01) |
| *A61B 17/88* | (2006.01) |
| *A61B 17/80* | (2006.01) |
| *A61B 17/17* | (2006.01) |
| *A61B 17/00* | (2006.01) |
| *A61B 17/90* | (2006.01) |

(52) U.S. Cl.
CPC .......... *A61B 17/88* (2013.01); *A61B 17/1728* (2013.01); *A61B 17/1789* (2016.11); *A61B 17/808* (2013.01); *A61B 17/8076* (2013.01); *A61B 17/8057* (2013.01); *A61B 17/90* (2021.08); *A61B 2017/00477* (2013.01)

(58) Field of Classification Search
USPC .................... 606/96–98, 148, 916
See application file for complete search history.

(56) References Cited

U.S. PATENT DOCUMENTS

| | | | |
|---|---|---|---|
| 5,190,545 A | 3/1993 | Corsi et al. | |
| 6,007,538 A | 12/1999 | Levin | |
| 7,588,576 B2 | 9/2009 | Teague et al. | |
| 8,414,594 B2 | 4/2013 | Berger et al. | |
| 10,307,193 B2 | 6/2019 | Garcia et al. | |
| 10,758,290 B2 | 9/2020 | Detweiler et al. | |
| 2006/0122597 A1* | 6/2006 | Jones ................. | A61B 17/7002 606/86 A |
| 2010/0274249 A1 | 10/2010 | Dell'Oca | |
| 2014/0039567 A1* | 2/2014 | Hoefer ............... | A61B 17/7082 606/86 A |

(Continued)

FOREIGN PATENT DOCUMENTS

| | | |
|---|---|---|
| JP | 3106821 U | 11/2004 |
| WO | 2017/156221 A1 | 9/2017 |

*Primary Examiner* — Sameh R Boles
(74) *Attorney, Agent, or Firm* — Schwegman Lundberg & Woessner, P.A.

(57) ABSTRACT

Implant positioning devices and fastener guides for implant positioning devices are disclosed for assisting in positioning orthopaedic fixation devices (such as bone plates, etc.). A fastener guide may include a body with slits in a first end of the body that form a guide arm proximal to the first end of the body. The guide arm is configured to releasably hold a fastener in the fastener guide. The fastener guide may also be coupled to a bone plate to facilitate ease of alignment and insertion of the fastener into a fastener apertures of the bone plate.

10 Claims, 35 Drawing Sheets

(56) References Cited

U.S. PATENT DOCUMENTS

2016/0051297 A1* 2/2016 Steffensmeier ...... A61B 17/808
  606/86 B
2016/0331420 A1* 11/2016 Dandanopoulos ..........................
  A61B 17/7082
2018/0177510 A1 6/2018 Whitaker et al.

* cited by examiner

IMPLANT POSITIONING DEVICES AND METHODS

CROSS REFERENCES TO RELATED APPLICATIONS

This application claims the benefit of U.S. Provisional Patent Application Ser. No. 62/564,037, filed Sep. 27, 2017, and entitled Single Implant Positioning Devices and Methods, the content of which is incorporated herein by reference in its entirety.

FIELD

The disclosure relates generally to implant positioning apparatuses and devices. More particularly, the disclosure relates to implant positioning apparatuses and devices for use in bone fixation, sternum fixation, and other orthopaedic fixation procedures.

BACKGROUND

In some surgical procedures involving bones, for instance, the procedure may involve separating a bone into portions, which are thereafter reunited. This happens, for example, in entries into the chest cavity, as for heart surgery, where the sternum is required to be separated along its length. There may be other instances where a bone has undergone fracturing through some trauma, and is thereafter to have portions rejoined for proper healing. Additionally, in applications involving the spine, there may be independent bones that benefit from holding a particular position relative to each other to allow for healing of the disc and other surrounding tissues.

The bones or skeletal tissue, or combinations of bone and tissue, can be held secure to one another in adjacency using a fixation device, or system. Many kinds of conventional fixation devices include wires or cables that are organized to pull the bone portions together, laterally across a divide or fracture. However, these types of fixation devices can be relatively complex to emplace. For instance, if a plate-type structure is to be attached to a bone, it is important to locate the fixation points (e.g., for screws) very accurately, as for drilling pilot holes for the screws. Plainly, speed and ease in then attaching the structure are significant considerations.

SUMMARY

Implant positioning devices and fastener guides for implant positioning devices are disclosed for assisting in positioning orthopaedic fixation devices (such as bone plates, etc.) for use in bone fixation, sternum fixation, and other orthopaedic fixation procedures. In an embodiment, a fastener guide for an orthopaedic fixation device includes a body and guide arms formed at a proximal end of the body. The guide arms are configured to releasably hold a fastener in the fastener guide such that a head of the fastener is exposed at a proximal end and engageable by a fastener driver.

In another embodiment, an orthopaedic fixation device is disclosed, wherein a plate is to be affixed to a bone. In this embodiment, the device includes a fastener guide releasably coupled to the plate and guide arms formed on a proximal end of a body of the fastener guide. The guide arms are configured to releasably hold a fastener in the fastener guide such that a head of the fastener is exposed at a proximal end and engageable by a fastener driver.

BRIEF DESCRIPTION OF THE DRAWINGS

Embodiments of devices, systems, and methods are illustrated in the figures of the accompanying drawings which are meant to be exemplary and not limiting, in which like references are intended to refer to like or corresponding parts, and in which.

DETAILED DESCRIPTION

While the embodiments described hereinafter are in the environment of positioning devices, systems and methods for use in positioning orthopaedic fixation devices for bones, it should be appreciated that the disclosure has broader application, such as other calcaneus body parts require fixation features, such as screws, pins, or other fastener, to be located and placed.

Figure 1:
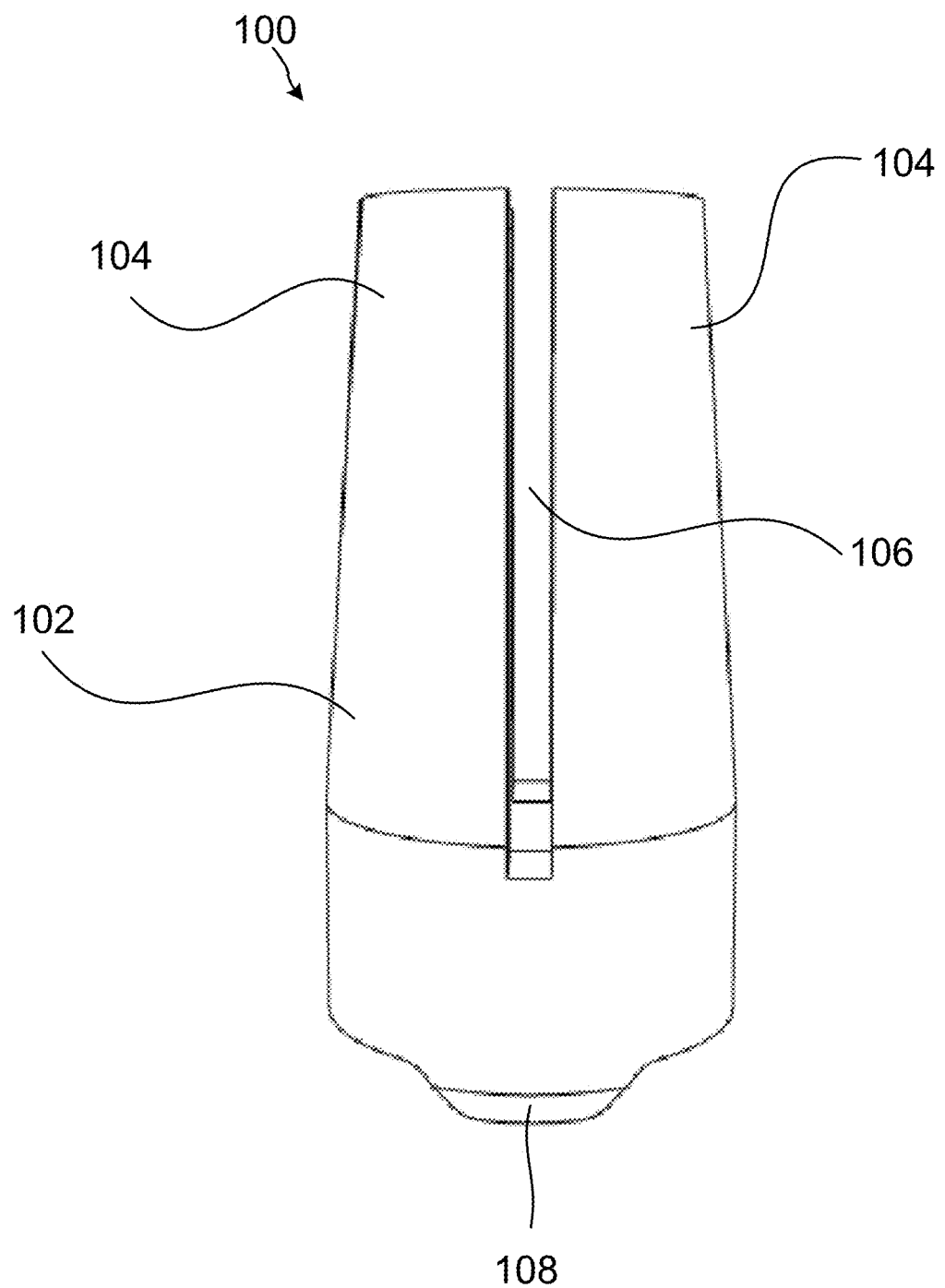
FIG. 1 illustrates a first perspective view of an implant positioning device in accordance with an embodiment of the disclosure.
Figure 2:
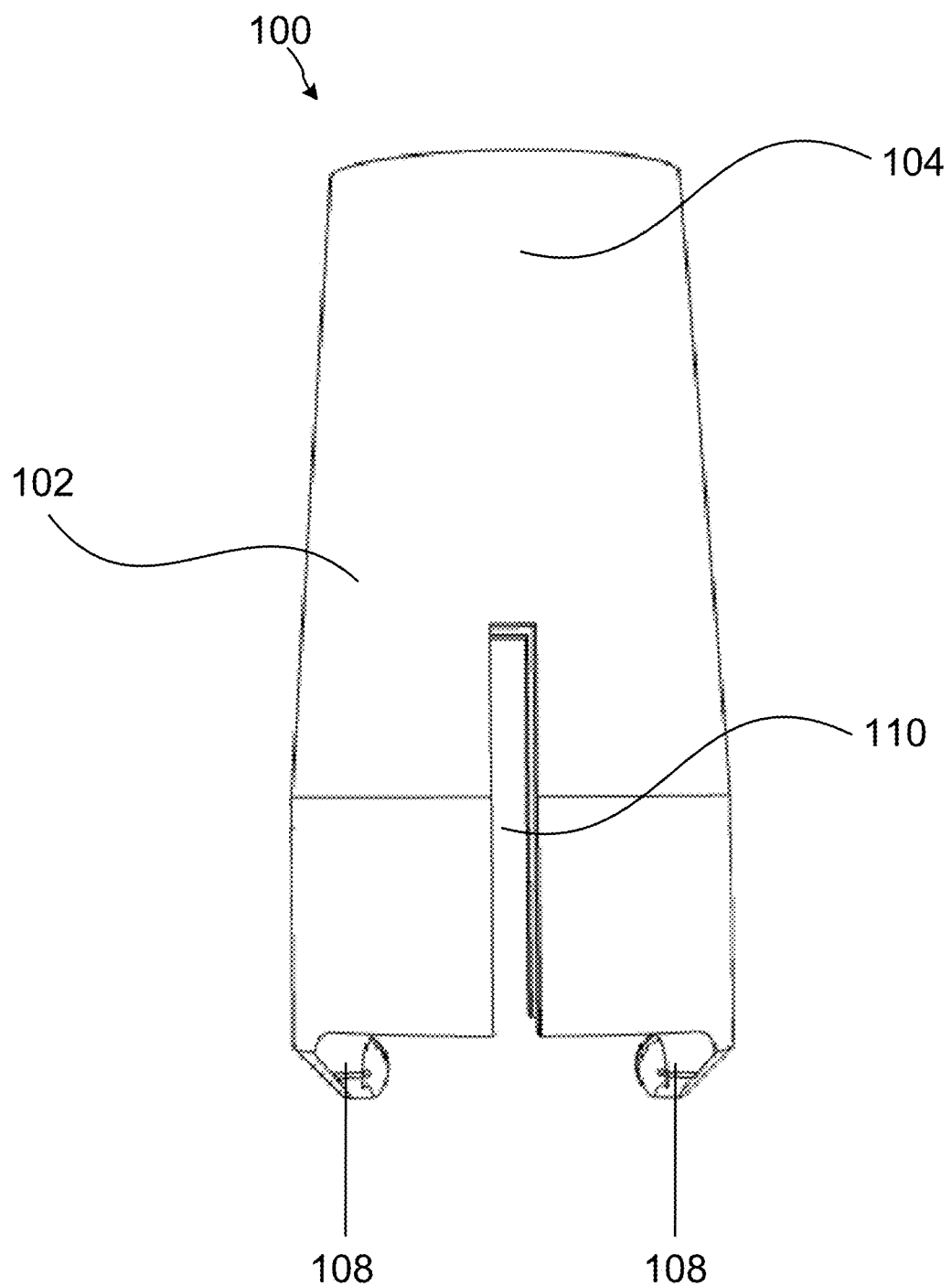
FIG. 2 illustrates a second perspective view of the implant positioning device of FIG. 1 in accordance with an embodiment of the disclosure.
Figure 3:
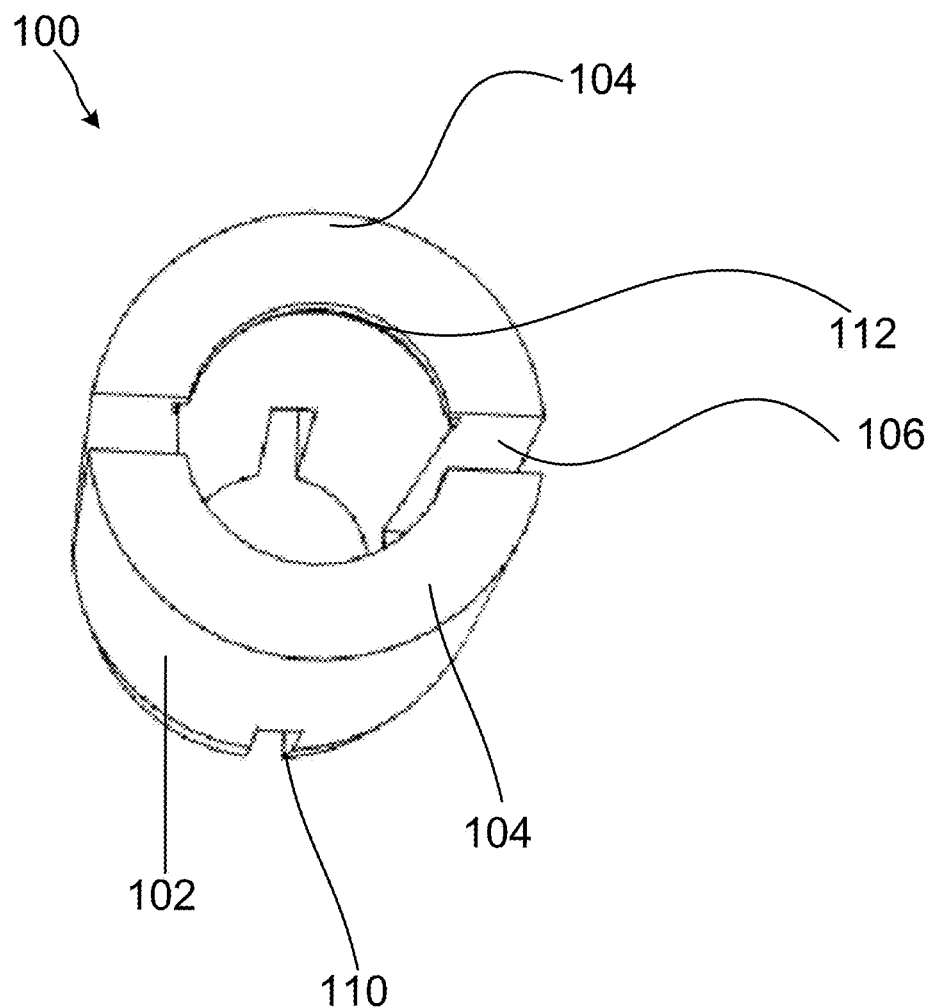
FIG. 3 illustrates a third perspective view of the implant positioning device of FIG. 1 in accordance with an embodiment of the disclosure.
Figure 4:
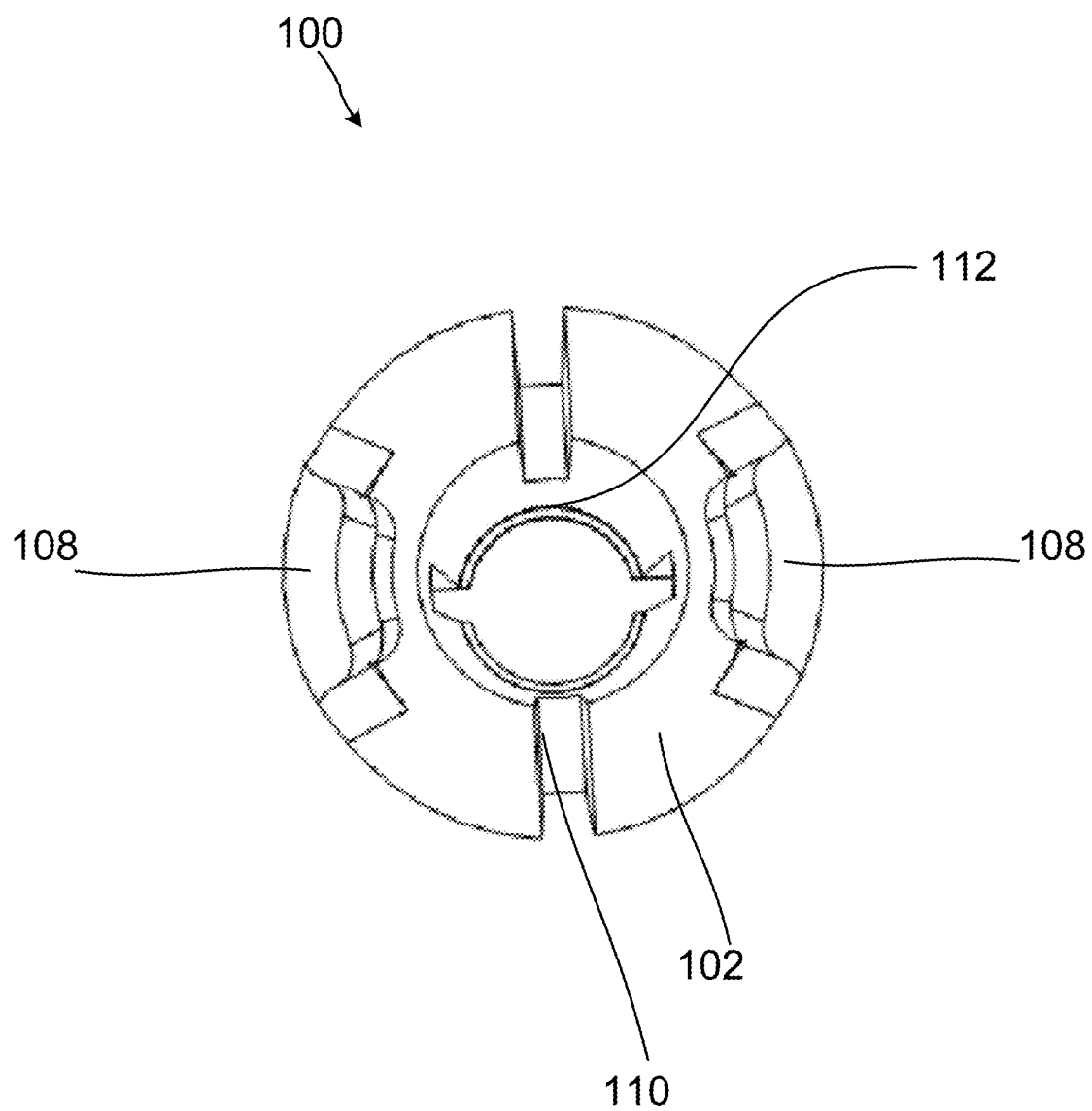
FIG. 4 illustrates a fourth perspective view of the implant positioning device of FIG. 1 in accordance with an embodiment of the disclosure.

FIGS. 1-7 illustrate a fastener guide 100 for use with an implant positioning device according to an embodiment of the disclosure. As illustrated in FIG. 1, the fastener guide 100 includes a frame or a body portion 102. The body portion 102 includes guide arms 104 (which may be finger-like structures) formed on a first end or proximal end of the fastener guide 100 by slits or apertures 106. The guide arms 104 are configured to releasably hold, guide, and position a fastener that may be used to couple an orthopaedic fixation device, such as a plate, to a bone or other body part. The proximal end of the fastener guide 100 also allows a top of the fastener to be exposed. This allows access for a fastener driver to access and engage a head of the fastener. The fastener may be a pin, rivet, and other type of fastener, etc., and the guide arms 104 and slits 106 may serve as expansion zones to help capture a wide variety of fasteners effectively. As illustrated, the slits 106 are positioned on opposing sides of the body 102, or displaced about 180 degrees with respect to each other around the body 102. The slits 106 also allow the guide arms 104 to elastically move or flex away from one another to allow the fastener to be moved or pushed through the fastener guide 100, when the fastener is driven into a bone or other body part.

As illustrated, the guide arms 104 may include two guide arms 104, however the body 102 may include more than two guide arms 104 to effectively hold a fastener and guide insertion of the fastener. The guide arms 104 may also be used to guide other instruments, for example, drills/drill bits, marking instruments to place markings, pegs, headless pins, etc. in a bone, which then serve as locating features to place plates or any other device before or after a resection is made, or after a fracture occurs.

In addition, the body portion 102 may include attachment arms 108 at a second end or distal end opposite the first/proximal end. The attachment arms 108 are configured to removably couple the fastener guide 100 to a plate 200, such that the fastener guide 100, or fastener disposed in the fastener guide 100, is in alignment with a fastener aperture 202 in the plate 200. While two attachment arms 108 are illustrated, the body 102 may have additional attachment arms 108 as needed, to removably couple the fastener guide 100 with the plate 200.

The body portion 102 may also have one or more second side apertures or slits 110. The second side apertures or slits 110 form one or more finger-like structures on the body. The second slits 110 may be disposed on opposite sides of the body 102 from each other, or displaced about 180 degrees with respect to each other around the body 102. The second slits 110 may also be displaced about 90 degrees with respect to the first slits 106. The second side apertures or slits 110 serve as expansion zones for the fastener guide 100 to removably couple with the plate 200. For example, the slits 110 allow the attachment arms 108 to elastically move or flex away from one another, and then move or flex back towards one another to allow the fastener guide 100 to be moved or pushed onto a bone plate. The second slits 110 may also allow for ease of cleaning and sterilization of the fastener guide 100.

According one aspect of the disclosure, the body 102 may have a substantially tubular shape. The fastener guide 100 may also include a ledge 112 extending inward from an inner tubular sidewall of the body 102 proximal to the first end of the fastener guide 100. The ledge 112 may be used to assist in holding the fastener in the fastener guide 100. According to a further aspect of the disclosure, the ledge 112 may include one or more flexible biasing elements disposed around the tubular side wall of the body 102. Multiple biasing elements may be used to help position the individual fastener in the proper orientation for insertion into a bone or other body part.

According to one aspect of the disclosure, the fastener guide 100 may be disposable, and pre-loaded with fasteners. Additionally, the body 102 may be made of a semi-elastic material such that the guide arms 104 and attachment arms 108 are able to expand without substantial deformation, such as plastic. Alternatively, the body 102 may be made of a metal material that allows the guide arms 104 and attachment arms 108 to expand without substantial deformation.

Figure 5:
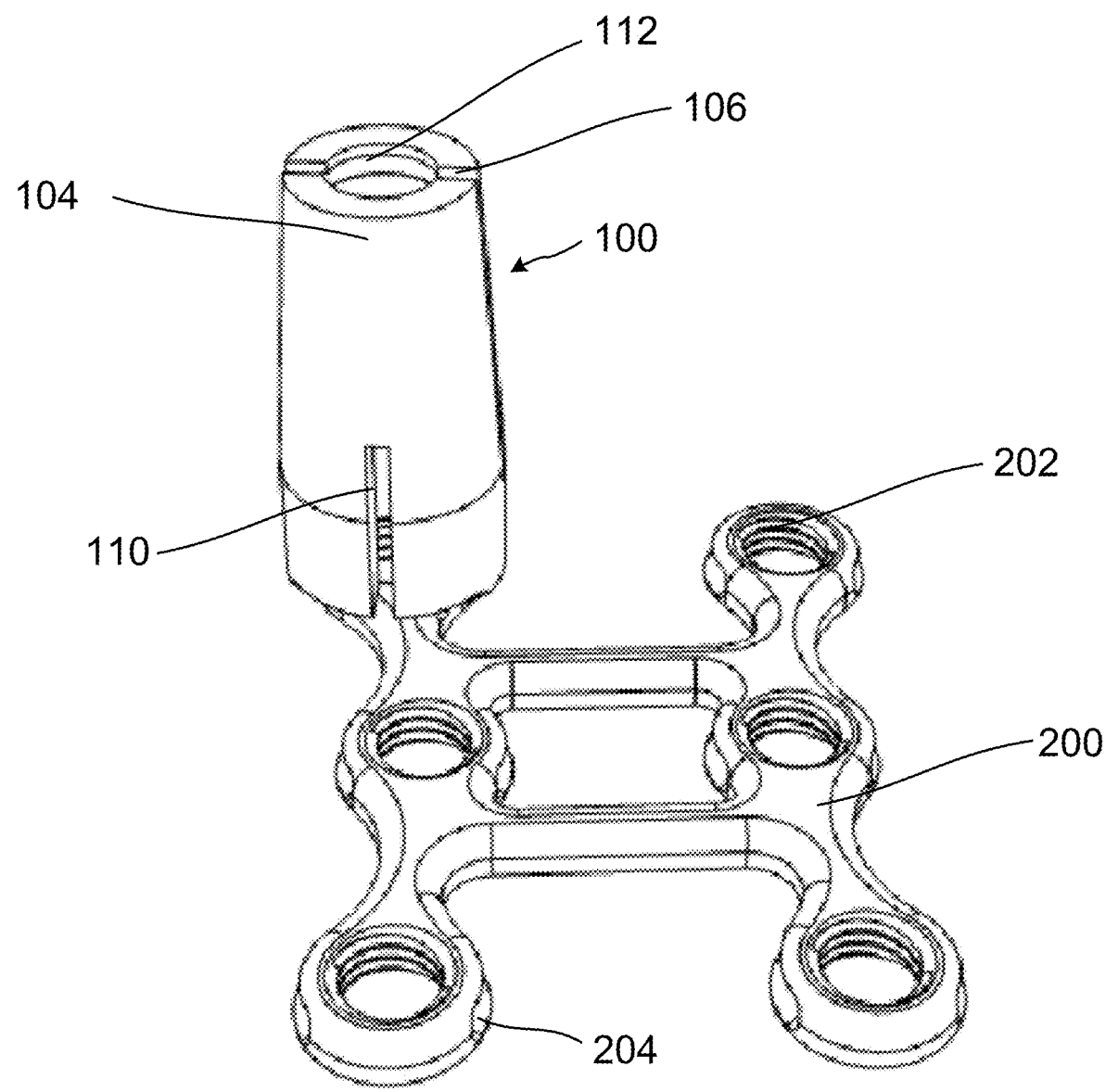
FIG. 5 illustrates a first perspective view of the implant positioning device of FIG. 1 aligned with a plate in accordance with an embodiment of the disclosure.
Figure 6:
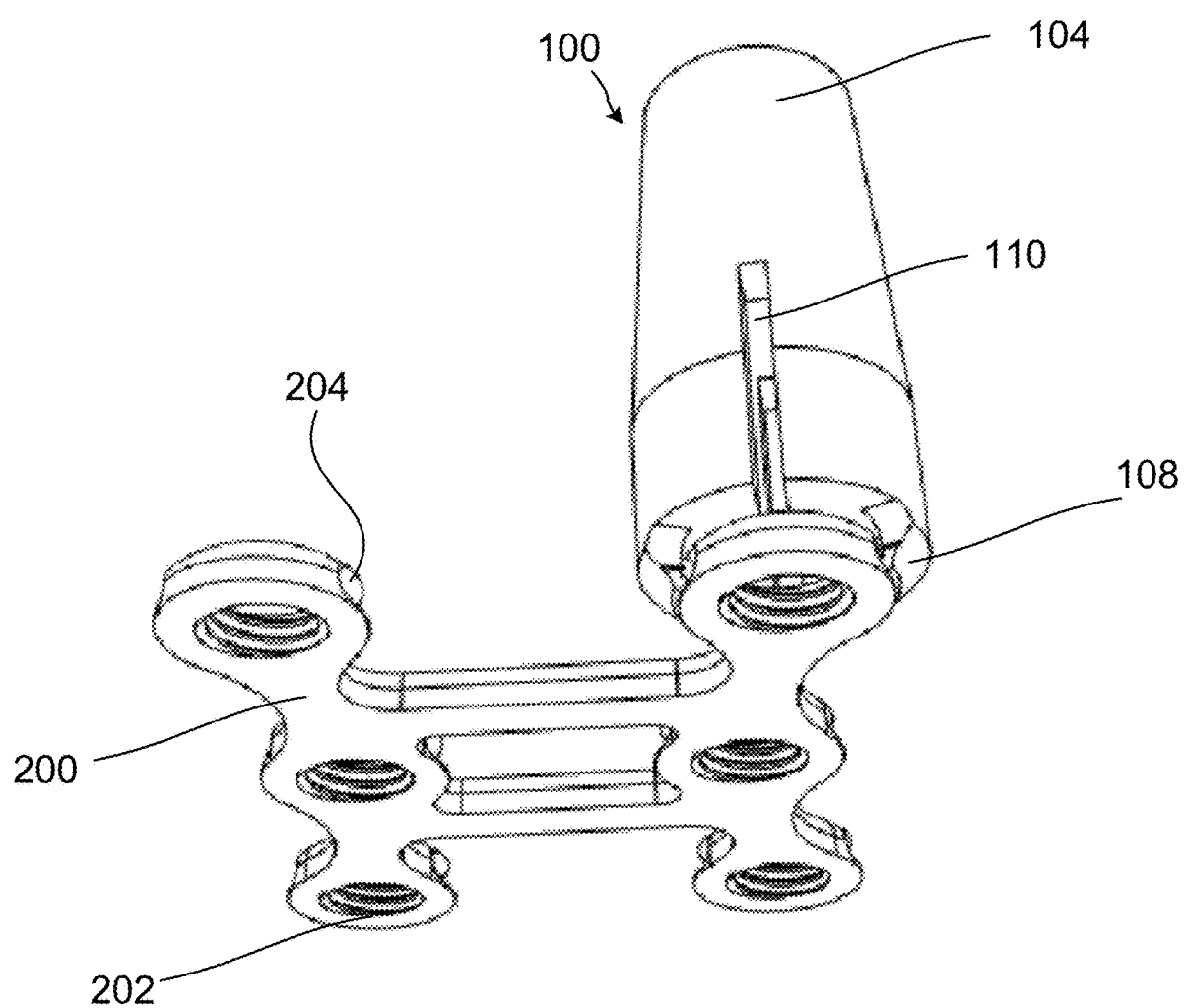
FIG. 6 illustrates a second perspective view of the implant positioning device of FIG. 1 aligned with the plate in accordance with an embodiment of the disclosure.
Figure 7:
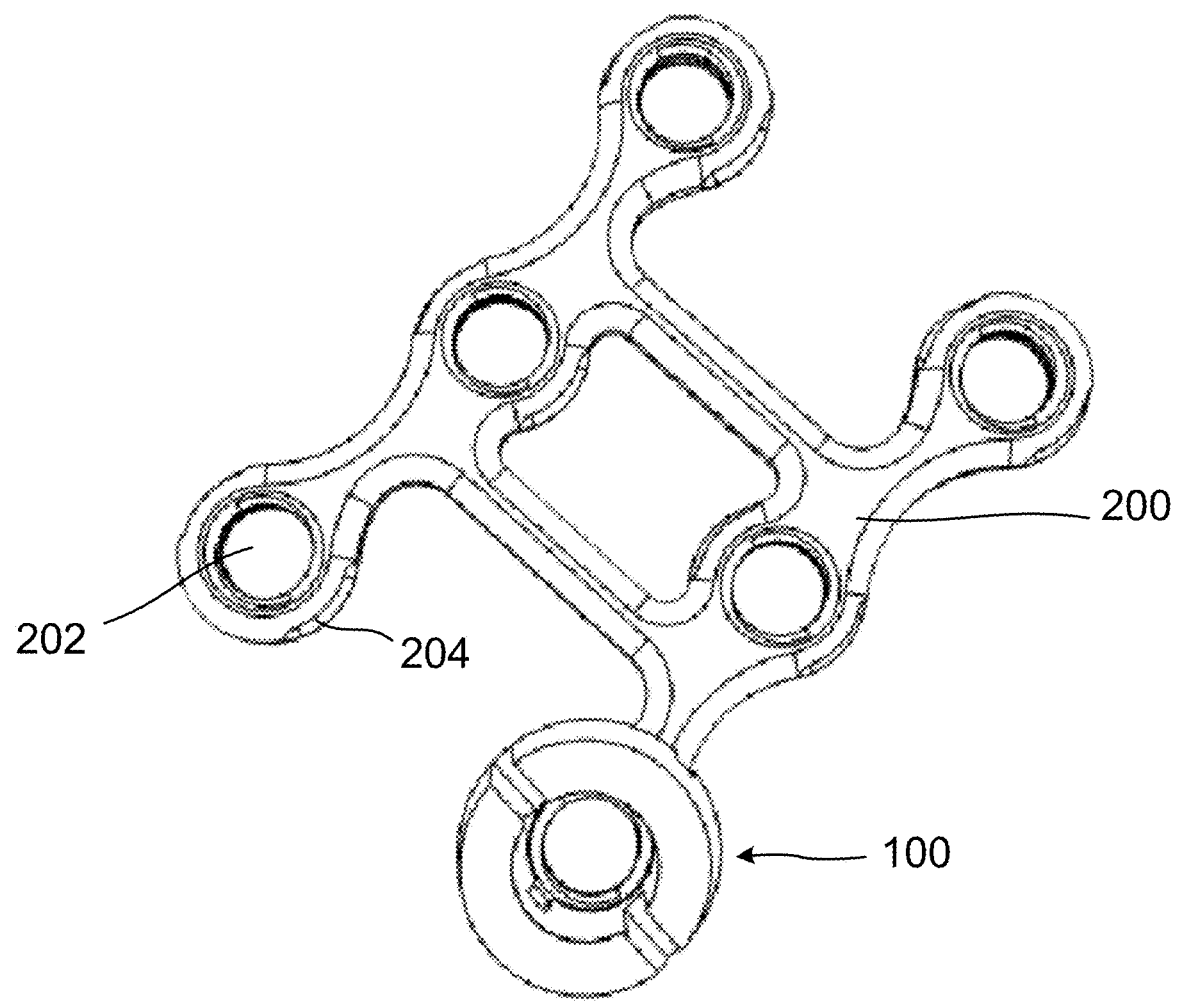
FIG. 7 illustrates a third perspective view of the implant positioning device of FIG. 1 aligned with the plate in accordance with an embodiment of the disclosure.

FIGS. 5-7 illustrate a plate 200 that is attachable to a bone. The plate 200 includes one or more fastener apertures 202, each with grooves 204 configured to receive the attachment arms 108 to couple the fastener guide 100 to the plate 200. For example, as shown in FIG. 6, each attachment arm 108 may be configured to fit within a groove 204 disposed on an outer portion of the fastener aperture 202 on the plate 200 to removably couple the fastener guide 100 to the plate 200.

In one example, the fastener guide 100 may be preloaded with a fastener by placing the fastener in the first end of the fastener guide 100. This may include pushing the fastener into the fastener guide 100 until a head of the fastener is gripped and held in place by the guide arms 104 and/or ledge 112. The fastener guide 100 may then be coupled to a plate, such as plate 200, by pushing the second end of the fastener guide 100 onto the plate 200. This may cause the attachment arms 108 to move or flex away from one another, and then snap towards one another into the respective grooves 204 of the plate 200. It should be appreciated that the fastener guide 100 may be coupled to a plate, such as plate 200, prior to the insertion of the fastener.

Once the fastener guide 100 is coupled to the plate 200 and the fastener is inserted into the fastener guide, the fastener guide 100 may provide a type of handle or holding zone that can be gripped by a user or other instrument. This allows the plate 200 to be positioned on a bone or other body part. Once positioned, the fastener can be driven through the fastener driver 100 and fastener aperture 202, and into the bone or other body part by a fastener driver to couple the plate 200 to the bone or other body part. As the fastener is driven through the fastener guide 100, the slits 106 allow the guide arms 104 to be moved or flexed away from one another to allow the fastener to move through the fastener guide 100.

It should be appreciated that a single fastener guide 100 can be coupled to the plate 200 in alignment with each one of the fastener apertures 202. This may facilitate ease of alignment and insertion of separate fasteners into each of the fastener apertures 202. It should also be appreciated that the size, shape, and number of fastener apertures of the plate can be modified and adapted for a specific application. Similarly, the fastener guide 100 may be adapted or modified to accommodate different plate geometries and features. The fastener guide 100 may be used in conjunction with any type of bone plate or other type of plate. For example, the fastener guide 100 may be used for alignment and fixation of boney elements to prevent motion in a particular direction as well as providing dynamic stabilization. The fastener guide 100 may also be used prior to or after a separation of a bone or other calcaneus body parts to align one or more plates.

Figure 8:
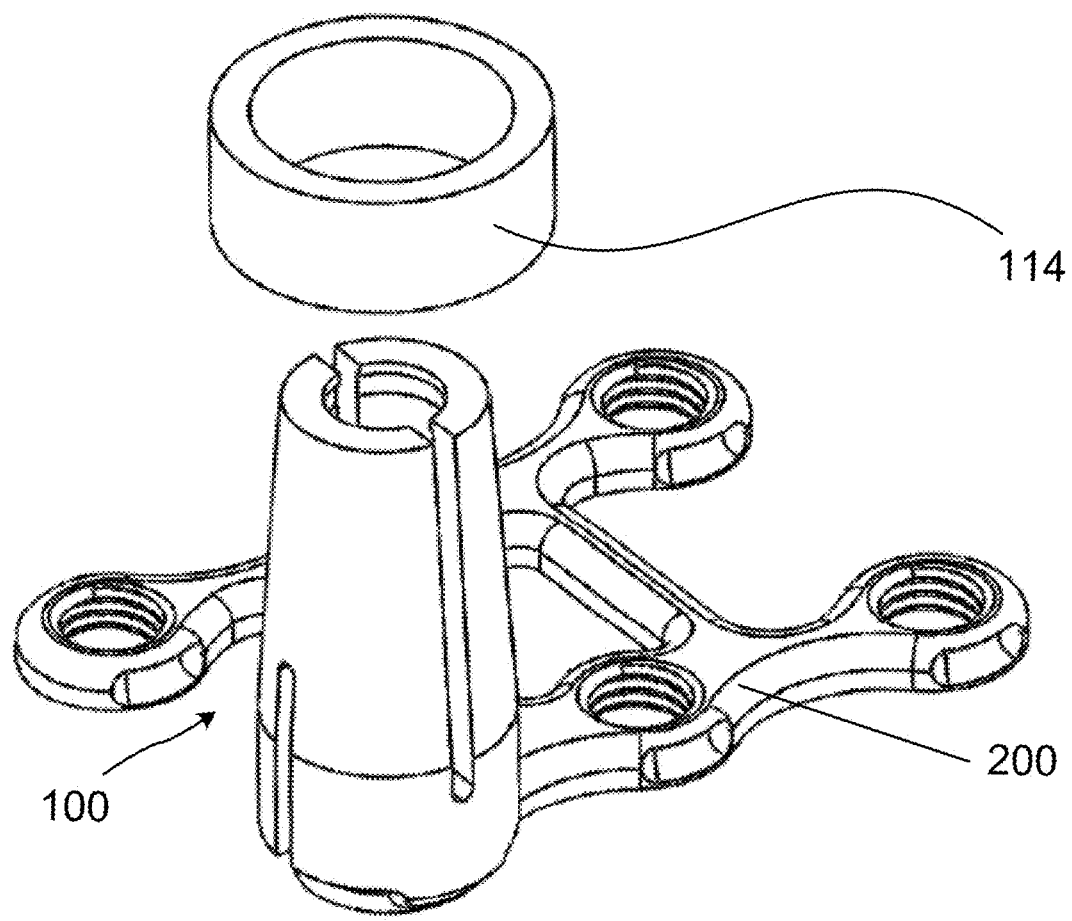
FIG. 8 illustrates a first perspective view of the implant positioning device of FIG. 1 aligned with a plate and a collar in accordance with an embodiment of the disclosure.
Figure 9:
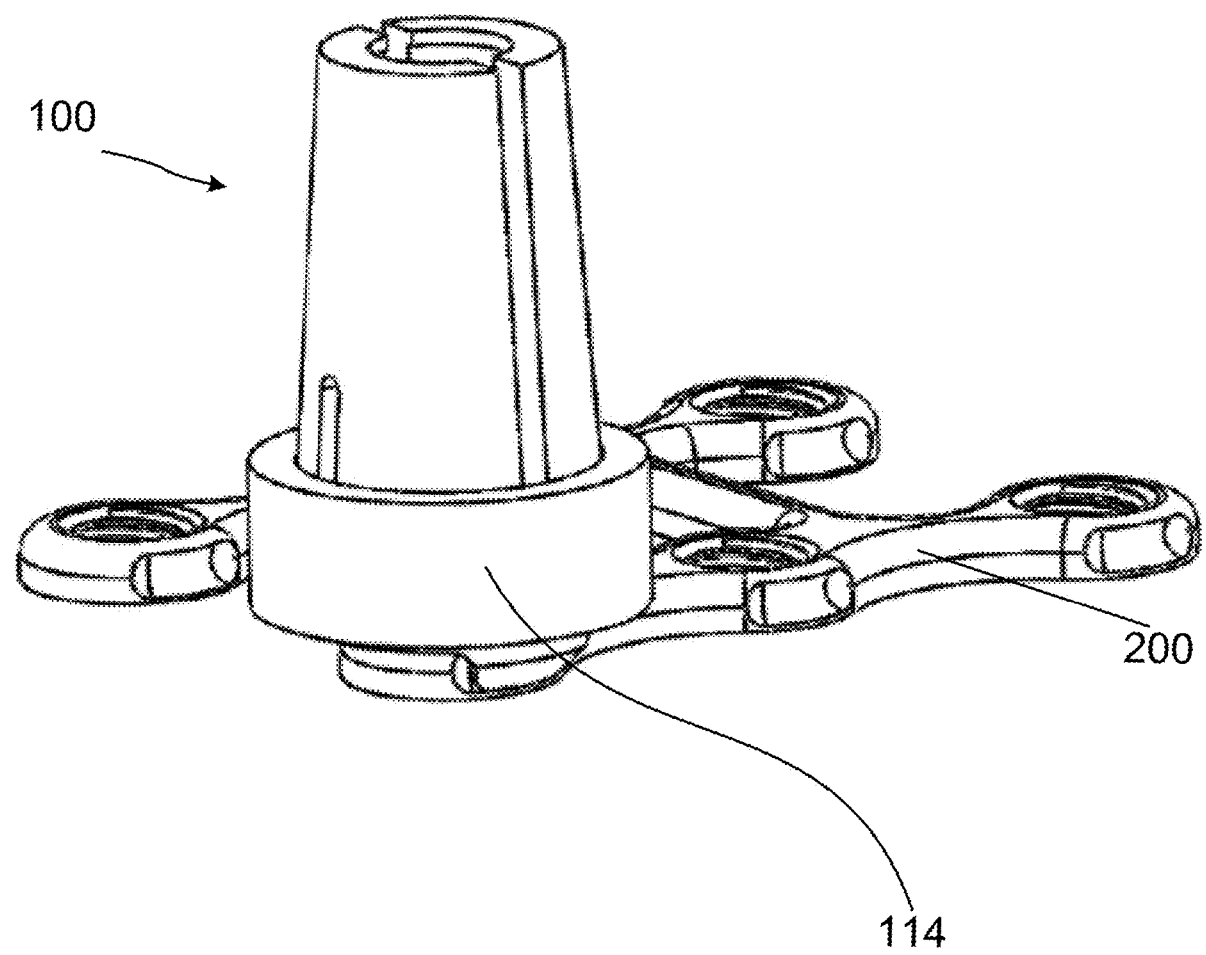
FIG. 9 illustrates a second perspective view of the implant positioning device of FIG. 1 aligned with a plate and a collar in accordance with an embodiment of the disclosure.

FIGS. 8-9 illustrate a collar 114 that may be coupled to the fastener guide 100 when the fastener guide 100 is coupled to the plate 200. The collar 114 may be configured to slide over a proximal end (or first end) of the fastener guide 100. The collar 114 may securely fit around the distal end (or second end) of the fastener guide 100 to minimize movement or flexing of the attachment arms 108 away from each other. This assists in minimizing the risk of the fastener guide 100 from accidentally decoupling from the plate 200.

Figure 10:
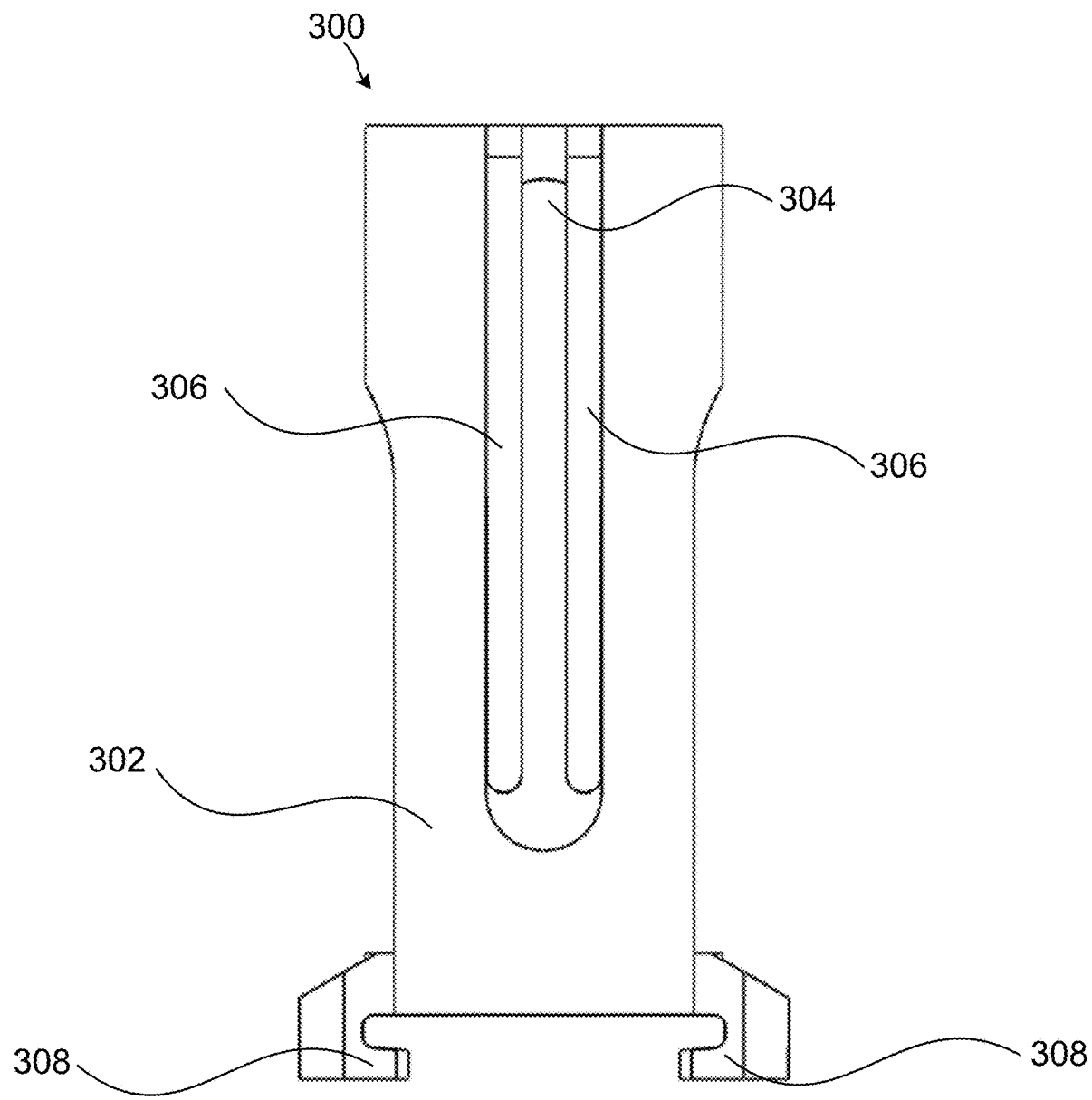
FIG. 10 illustrates a first perspective view of an implant positioning device in accordance with an embodiment of the disclosure.

FIGS. 10-16 illustrate a fastener guide 300 for use with an implant positioning device according to a further embodiment of the disclosure. As illustrated in FIG. 10, the fastener guide 300 includes a frame or a body portion 302. The body portion 302 includes a guide arm 304 (which may be a finger-like structure) formed on a first end or proximal end of the fastener guide 300 by slits or apertures 306. The guide arm 304 is configured to releasably hold, guide, and position a fastener that may be used to couple an orthopaedic fixation device, such as a plate, to a bone or other body part. The proximal end of the fastener guide 300 also allows a top of the fastener to be exposed. This allows access for a fastener driver to access and engage a head of the fastener. The fastener may be a pin, rivet, and other type of fastener, etc., and the guide arm 304 may serve as expansion zones to help capture a wide variety of fasteners effectively.

In this embodiment, the slits 306 may be disposed on opposite sides of the guide arm 304. By having the slits 306 disposed on opposite sides of the guide arm 304, the guide arm 304 is allowed to elastically move or flex away from the body 302 to allow the fastener to be moved or pushed through the fastener guide 300, when the fastener is driven into a bone or other body part. Additionally, the guide arm 304 and the slits 306 may be disposed on the body 302 such that the guide arm 304 is recessed within an outer circumference of the body 302. The guide arm 304 may also have a thickness less than a thickness of the body 302. For example, as shown in FIG. 10, the guide arm 304 and the slits 306 may be disposed in an upper groove on the body 302. Further, the groove may extend from the proximal end towards the distal end.

As illustrated, the guide arm 304 may include one guide arm 304, however the body 302 may include more than guide arm 304 to effectively hold a fastener and guide insertion of the fastener. The body 302 and guide arm 304 may also be used to guide other instruments, for example, drills/drill bits, marking instruments to place markings, pegs, headless pins, etc. in a bone, which then serve as locating features to place plates or any other device before or after a resection is made, or after a fracture occurs.

The body portion 302 may also include attachment arms 308 at a second end or distal end opposite the first/proximal end. The attachment arms 308 are configured to removably couple the fastener guide 300 to a plate 400, such that the fastener guide 300, or fastener disposed in the fastener guide 300, is in alignment with a fastener aperture 402 in the plate 400. While two attachment arms 308 are illustrated, the body 302 may have additional attachment arms 308 as needed, to removably couple the fastener guide 300 with the plate 400.

The body portion 302 may also have one or more second side apertures or slits 310. The second side apertures or slits 310 form one or more finger-like structures on the body (such as the attachment arms 308). A first pair of second slits 310 may be disposed on opposite sides of one of the attachment arms 308, and another pair of second slits 310 may be disposed on opposite sides of the other of the attachment arms 308. The second side apertures or slits 310 serve as expansion zones for the fastener guide 300 to removably couple with the plate 400. For example, the slits 310 allow the attachment arms 308 to elastically move or flex away from one another, and then move or flex back towards one another to allow the fastener guide 300 to be moved or pushed onto a bone plate.

Figure 11:
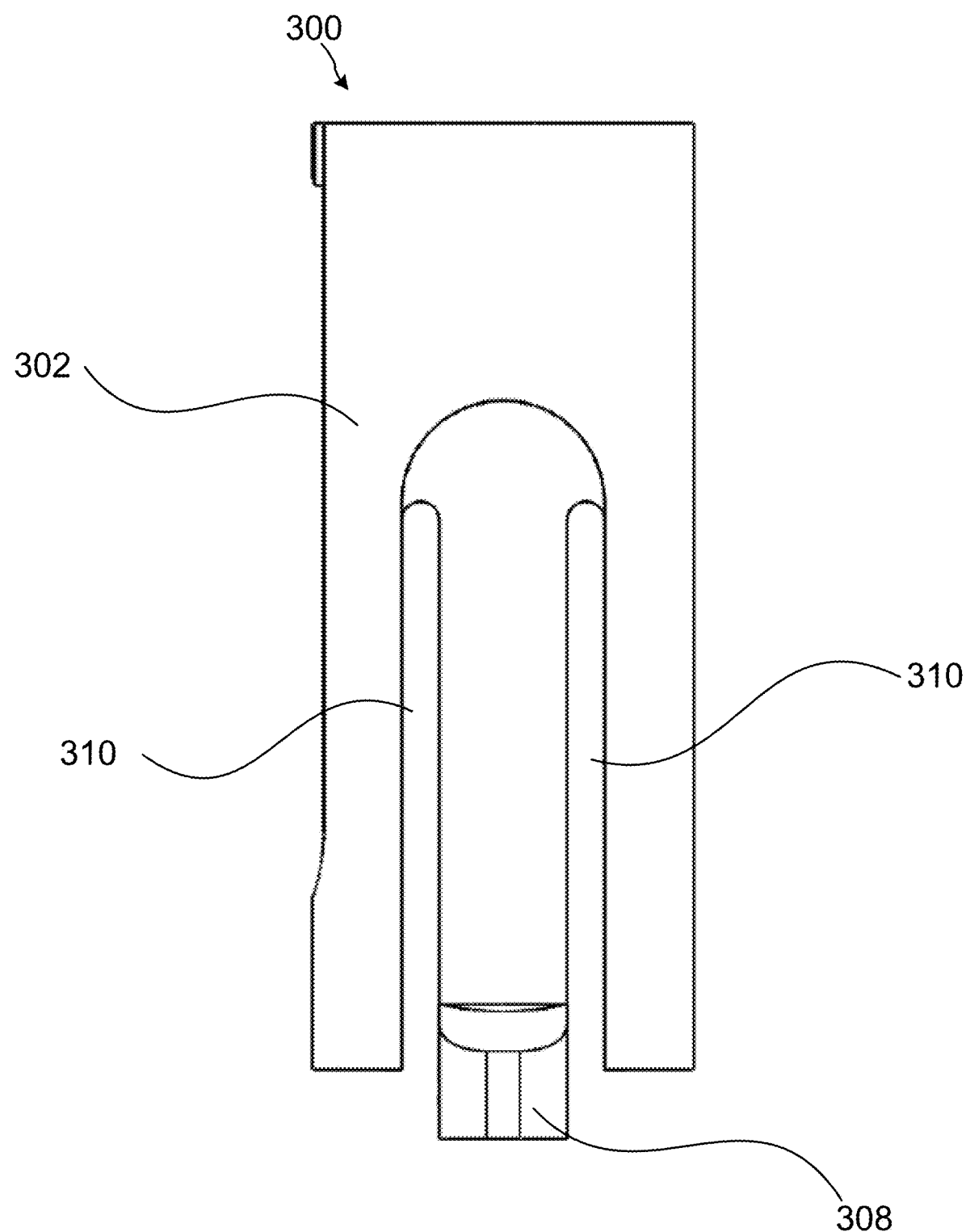
FIG. 11 illustrates a second perspective view of the implant positioning device of FIG. 10 in accordance with an embodiment of the disclosure.
Figure 12:
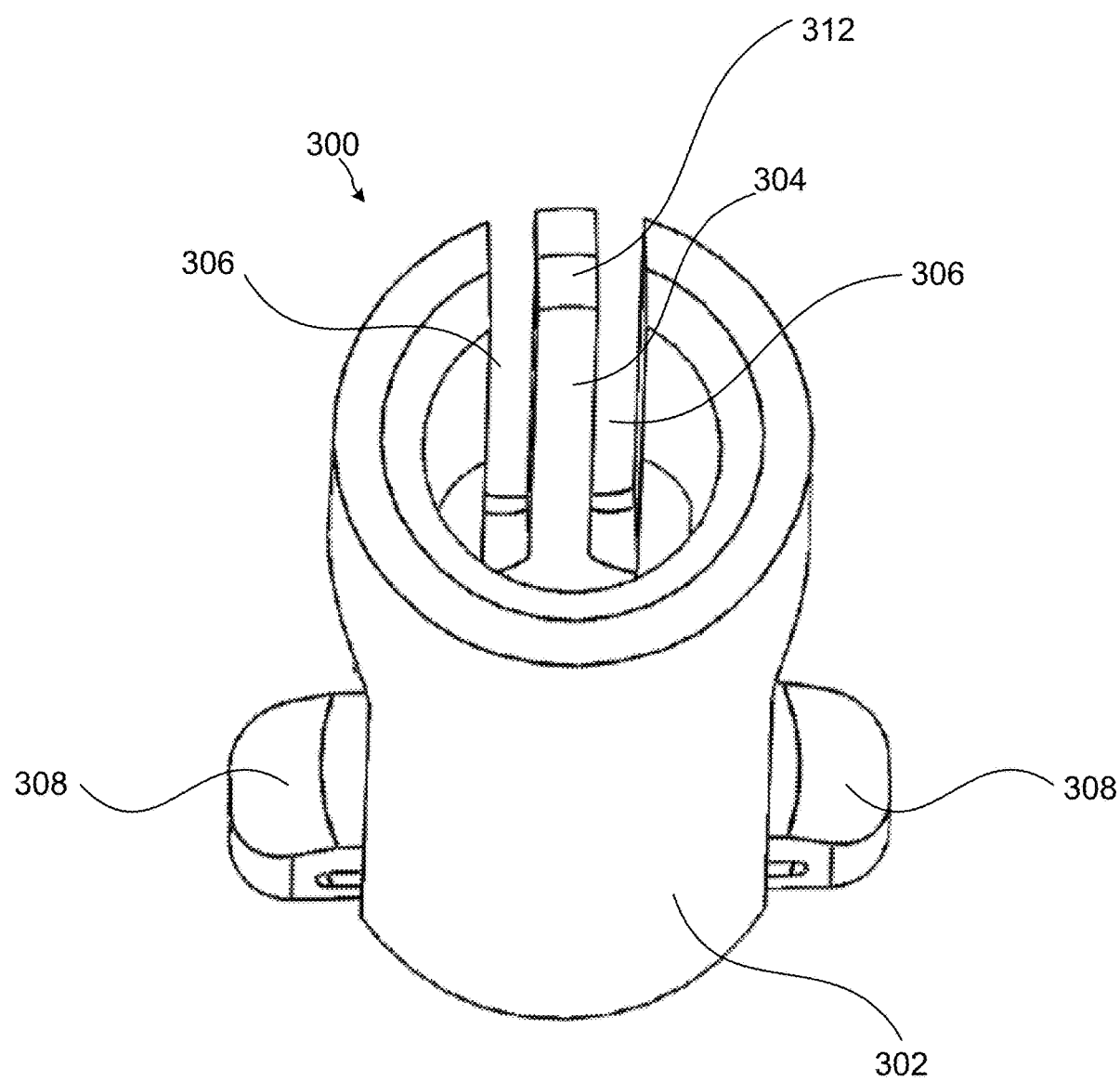
FIG. 12 illustrates a third perspective view of the implant positioning device of FIG. 10 in accordance with an embodiment of the disclosure.
Figure 13:
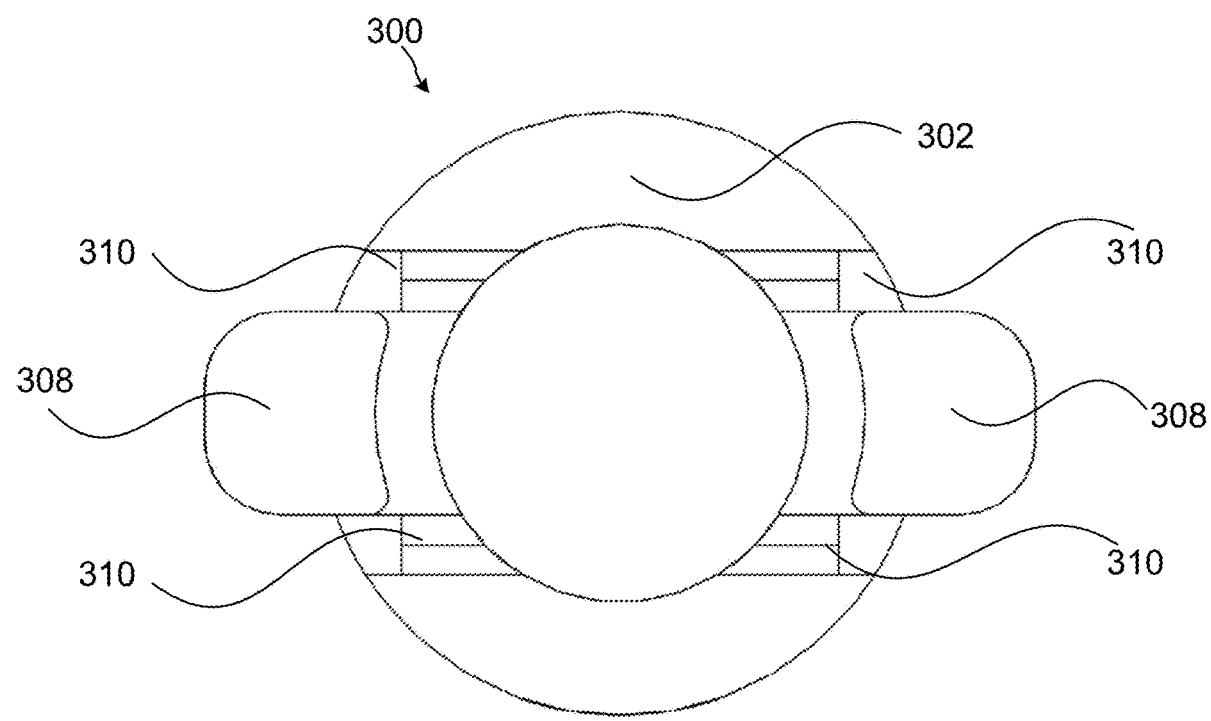
FIG. 13 illustrates a fourth perspective view of the implant positioning device of FIG. 10 in accordance with an embodiment of the disclosure.

The attachment arms 308 and the second slits 310 may be disposed on the body 302 such that the attachment arms 308 are recessed within an outer circumference of the body 302. The attachment arms 308 may also have a thickness less than a thickness of the body 302. For example, as shown in FIG. 11, the upper portion of the attachment arms 308 and the slits 310 may be disposed in lower grooves on the body 302. Further, the groove may extend from the distal end towards the proximal end.

According one aspect of the disclosure, the body 302 may have a substantially tubular shape. The fastener guide 300/guide arm 304 may also include protrusion 312 extending into an inner diameter of the body 302 proximal to the first end of the fastener guide 300. The protrusion 312 may be formed by deformation of the end of the guide arm 304 and used to assist in holding the fastener in the fastener guide 300 via a friction force or spring force caused by the guide arm 304. According to a further aspect of the disclosure, the fastener guide 300/guide arm 304 may include a ledge extending inward from an inner tubular sidewall of the body 302 proximal to the first end of the fastener guide 300. The ledge and/or protrusion 312 may include one or more flexible biasing elements disposed around the tubular side wall of the body 302. Multiple biasing elements may be used to help position the individual fastener in the proper orientation for insertion into a bone or other body part.

According to one aspect of the disclosure, the body 302 may be made of a metal material that allows the guide arm 304 and attachment arms 308 to flex without substantial deformation. In addition, the fastener guide 300 may be sterilizeable and reusable in multiple orthopaedic fixation procedures. Further, the fastener guide 300 may also be pre-loaded with fasteners.

Figure 14:
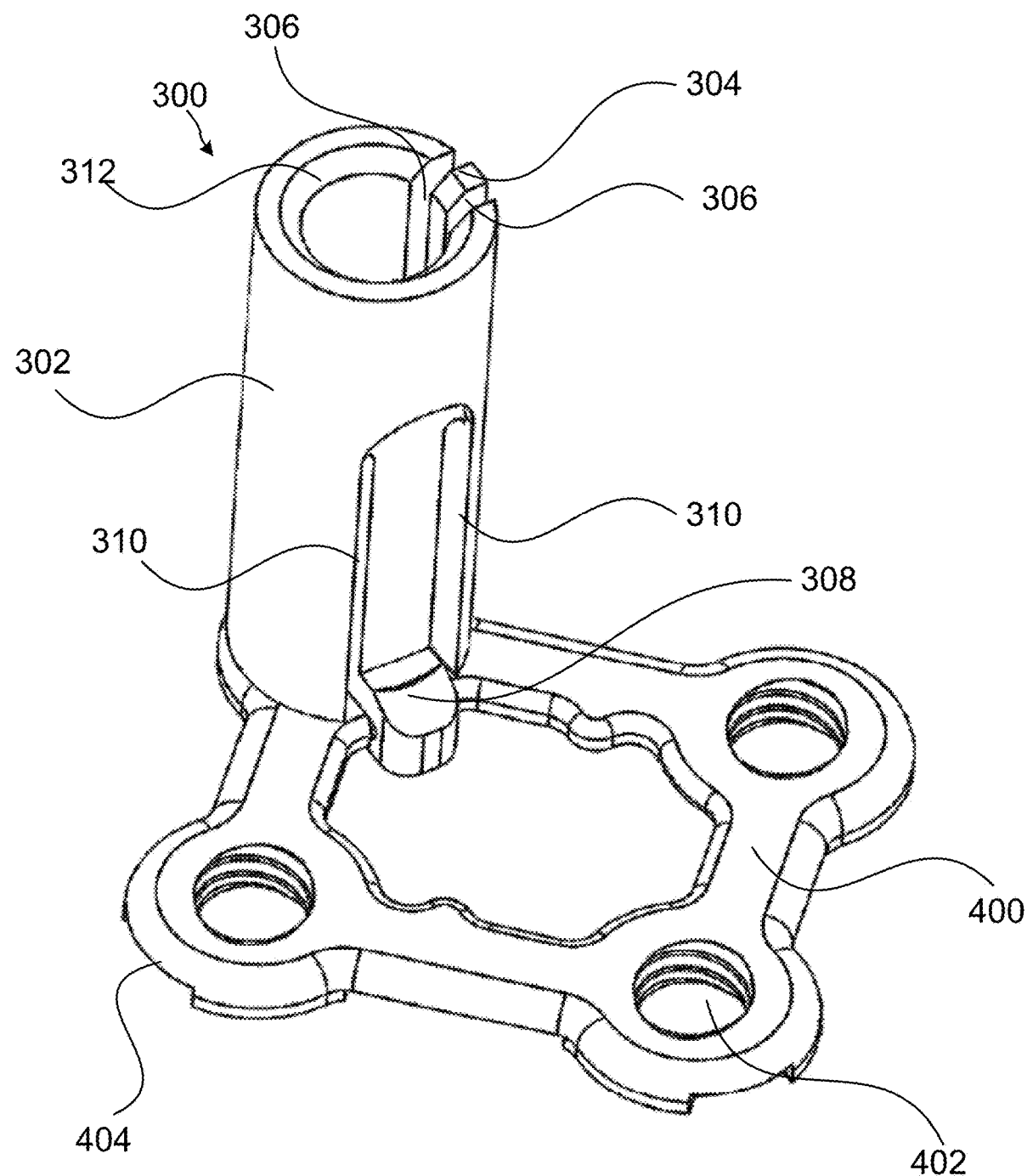
FIG. 14 illustrates a first perspective view of the implant positioning device of FIG. 10 aligned with a plate in accordance with an embodiment of the disclosure.
Figure 15:
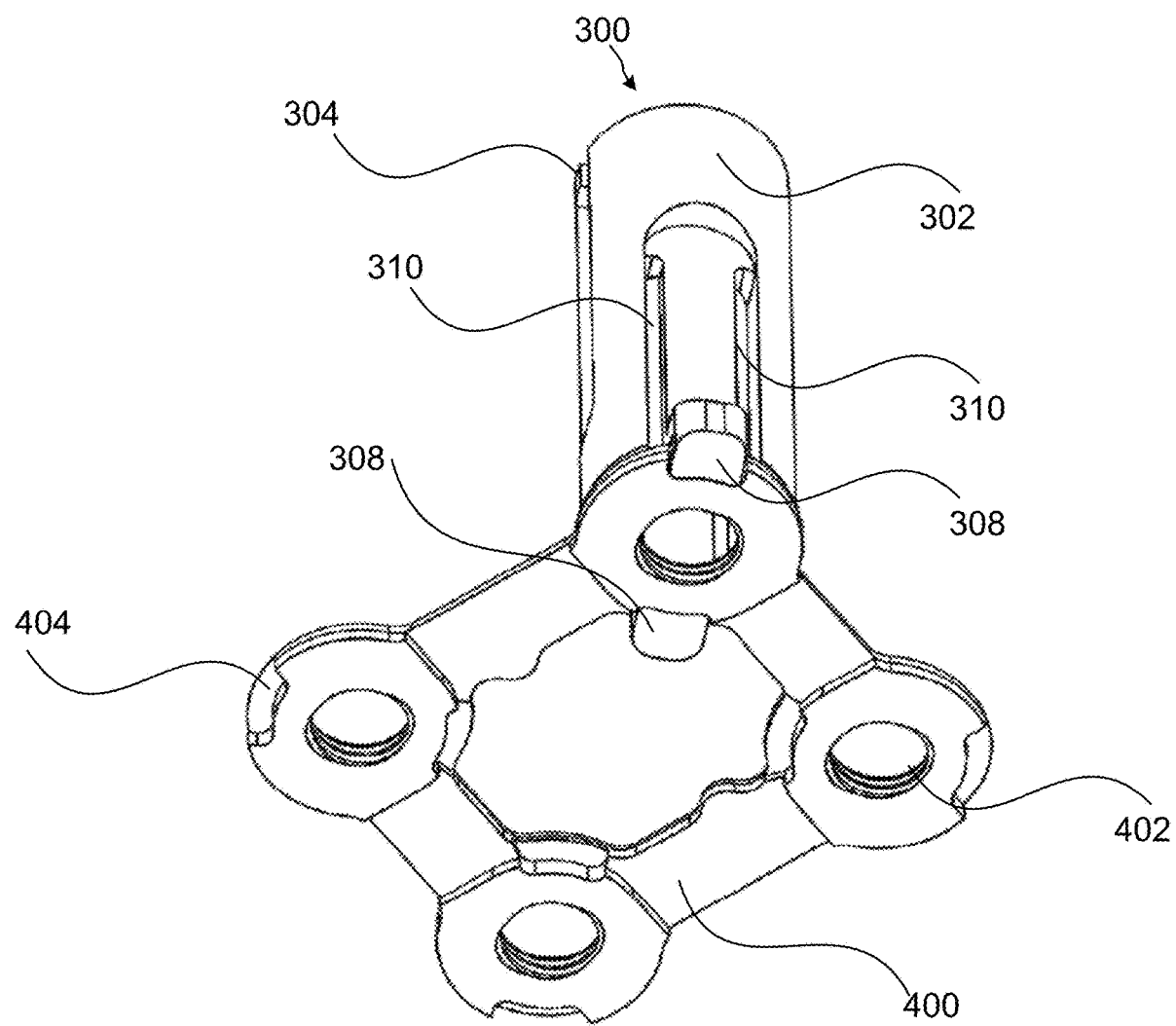
FIG. 15 illustrates a second perspective view of the implant positioning device of FIG. 10 aligned with the plate in accordance with an embodiment of the disclosure.
Figure 16:
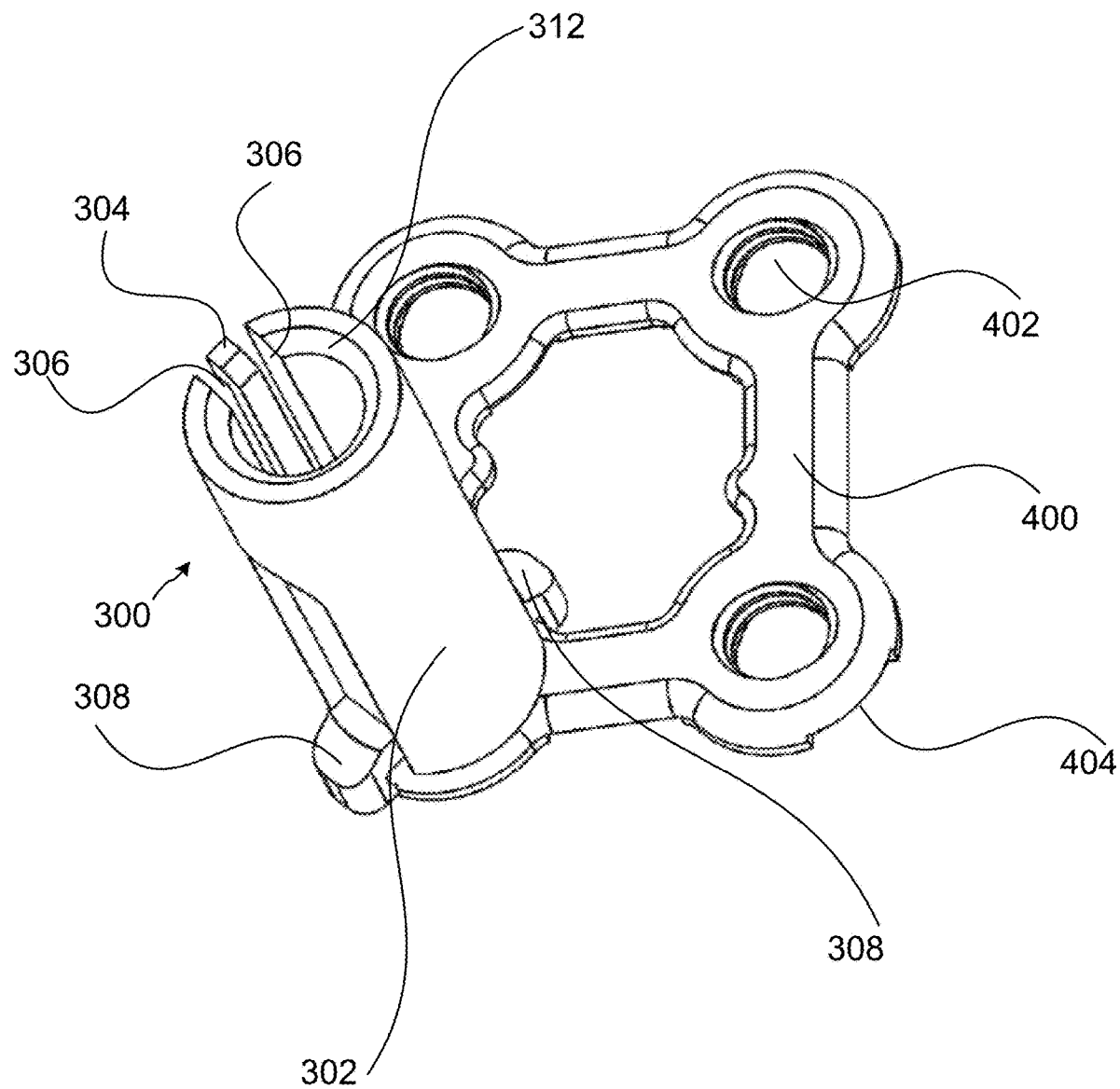
FIG. 16 illustrates a third perspective view of the implant positioning device of FIG. 10 aligned with the plate in accordance with an embodiment of the disclosure.

FIGS. 14-16 illustrate a plate 400 that is attachable to a bone. The plate 400 includes one or more fastener apertures 402, each with grooves 404 configured to receive the attachment arms 308 to couple the fastener guide 300 to the plate 400. For example, as shown in FIG. 15, each attachment arm 308 may be configured to fit within a groove 404 disposed on a bottom portion of the plate 400 to removably couple the fastener guide 300 to the plate 400.

In one example, the fastener guide 300 may be preloaded with a fastener by placing the fastener in the first end of the fastener guide 300. This may include pushing the fastener into the fastener guide 300 until a head of the fastener is gripped and held in place by the guide arm 304 and/or ledge 312. The fastener guide 300 may then be coupled to a plate, such as plate 400, by pushing the second end of the fastener guide 300 onto the plate 400. This may cause the attachment arms 308 to move or flex away from one another, and then snap towards one another into the respective grooves 404 of the plate 400. It should be appreciated that the fastener guide 300 may be coupled to a plate, such as plate 400, prior to the insertion of the fastener.

Once the fastener guide 300 is coupled to the plate 400 and the fastener is inserted into the fastener guide, the fastener guide 300 may provide a type of handle or holding zone that can be gripped by a user or other instrument. This allows the plate 400 to be positioned on a bone or other body part. Once positioned, the fastener can be driven through the fastener guide 300 and fastener aperture 402, and into the bone or other body part by a fastener driver to couple the plate 400 to the bone or other body part. As the fastener is driven through the fastener guide 300, the slits 306 allow the guide arm 304 to be moved or flexed away from the body 302 to allow the fastener to move through the fastener guide 300.

It should be appreciated that a single fastener guide 300 can be coupled to the plate 400 in alignment with each one of the fastener apertures 402. This may facilitate ease of alignment and insertion of separate fasteners into each of the fastener apertures 402. It should also be appreciated that the size, shape, and number of fastener apertures of the plate 400 can be modified and adapted for a specific application. Similarly, the fastener guide 300 may be adapted or modified to accommodate different plate geometries and features. The fastener guide 300 may be used in conjunction with any type of bone plate or other type of plate. For example, the fastener guide 300 may be used for alignment and fixation of boney elements to prevent motion in a particular direction as well as providing dynamic stabilization. The fastener guide 300 may also be used prior to or after a separation of a bone or other calcaneus body parts to align one or more plates.

Figure 17:
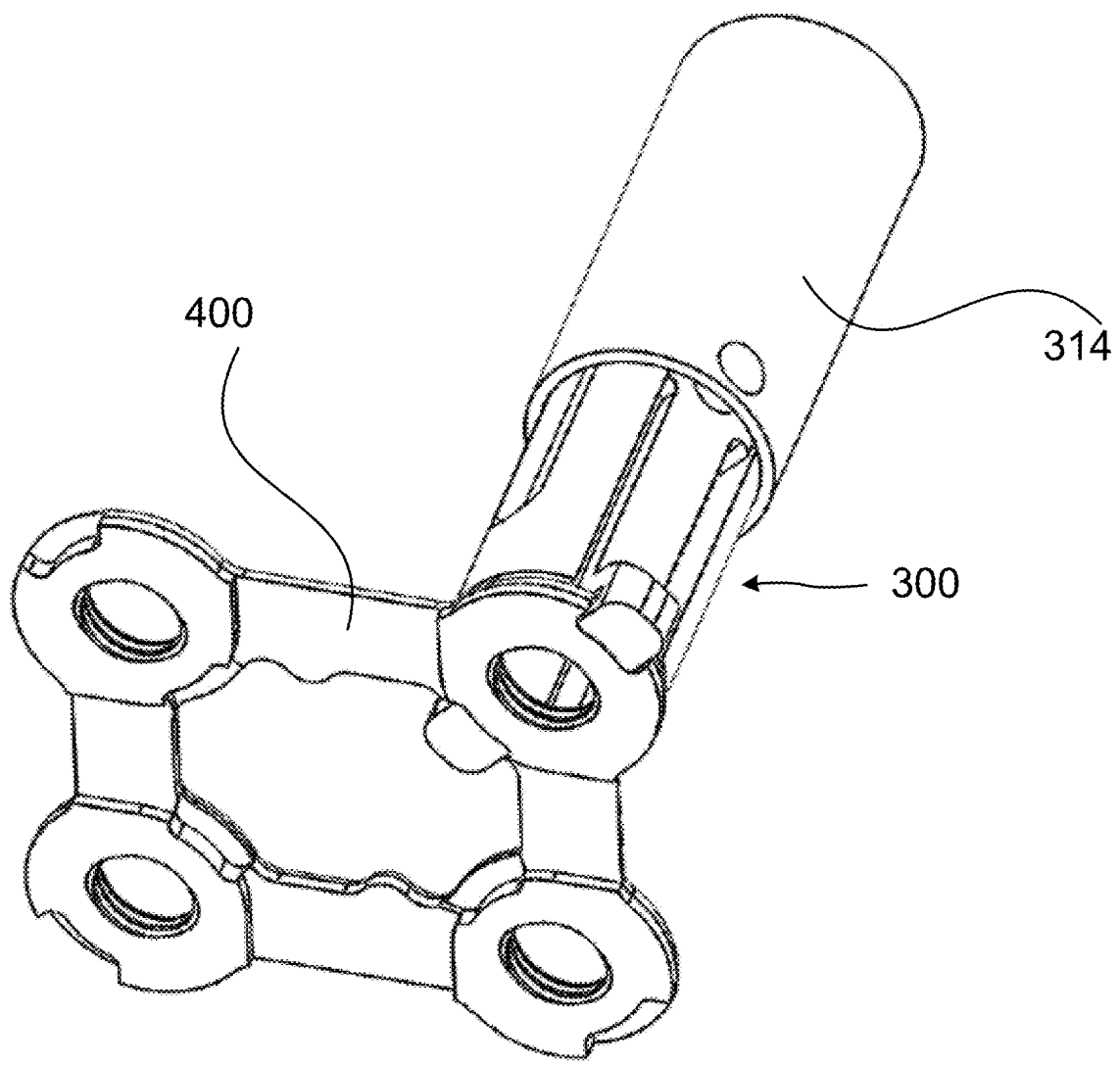
FIG. 17 illustrates a first perspective view of the implant positioning device of FIG. 10 aligned with a plate and a collar in accordance with an embodiment of the disclosure.
Figure 18:
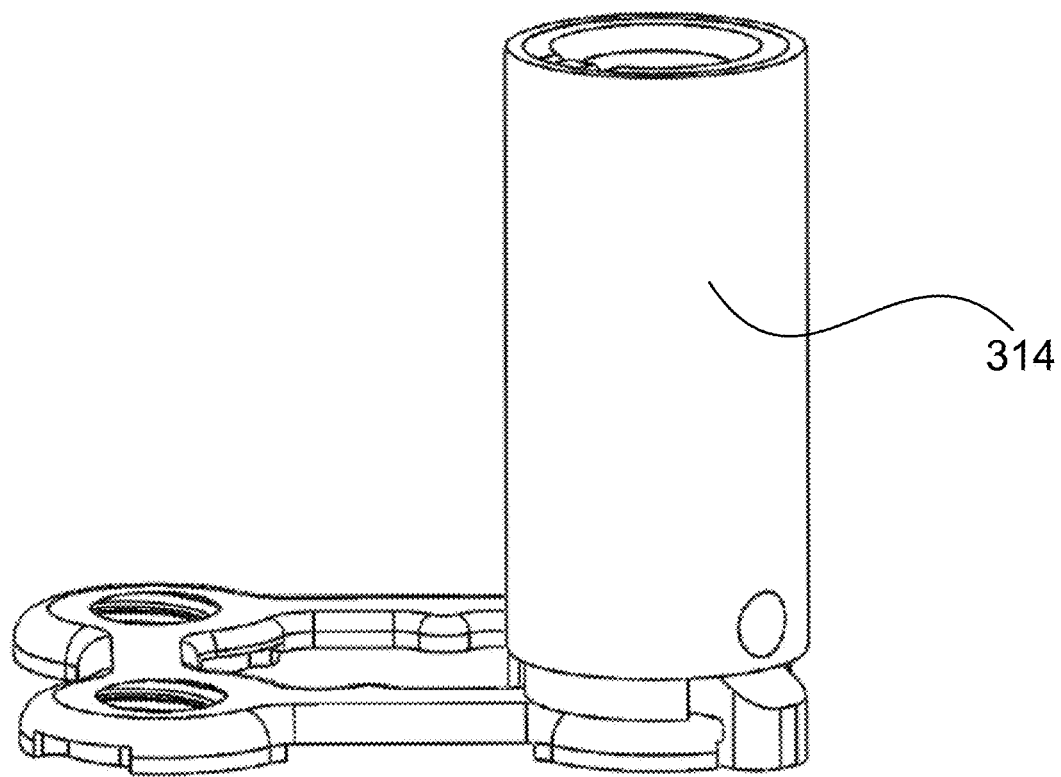
FIG. 18 illustrates a second perspective view of the implant positioning device of FIG. 10 aligned with a plate and a collar in accordance with an embodiment of the disclosure.
Figure 19:
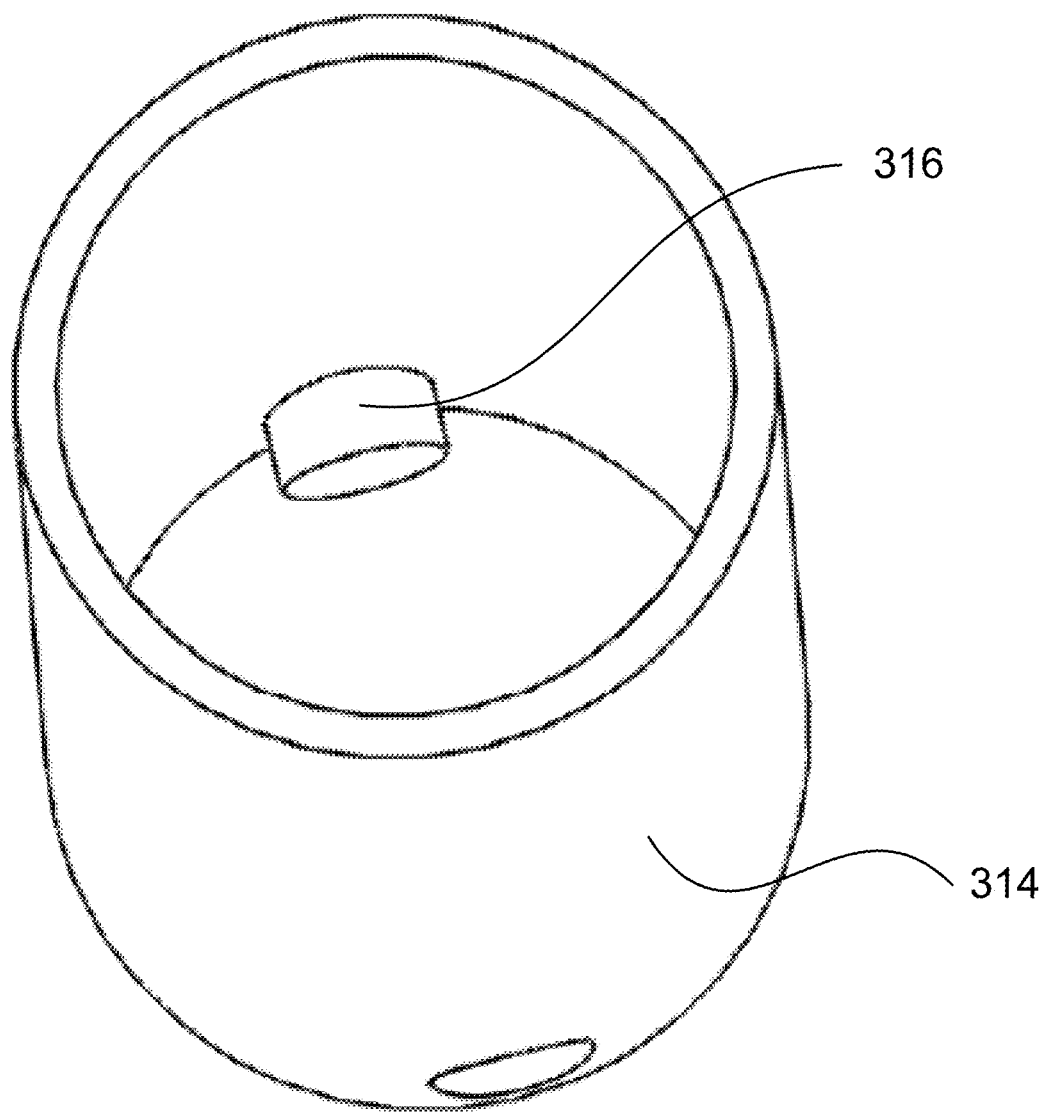
FIG. 19 illustrates a first perspective view a collar for the implant positioning device of FIG. 10 in accordance with an embodiment of the disclosure.
Figure 20A:
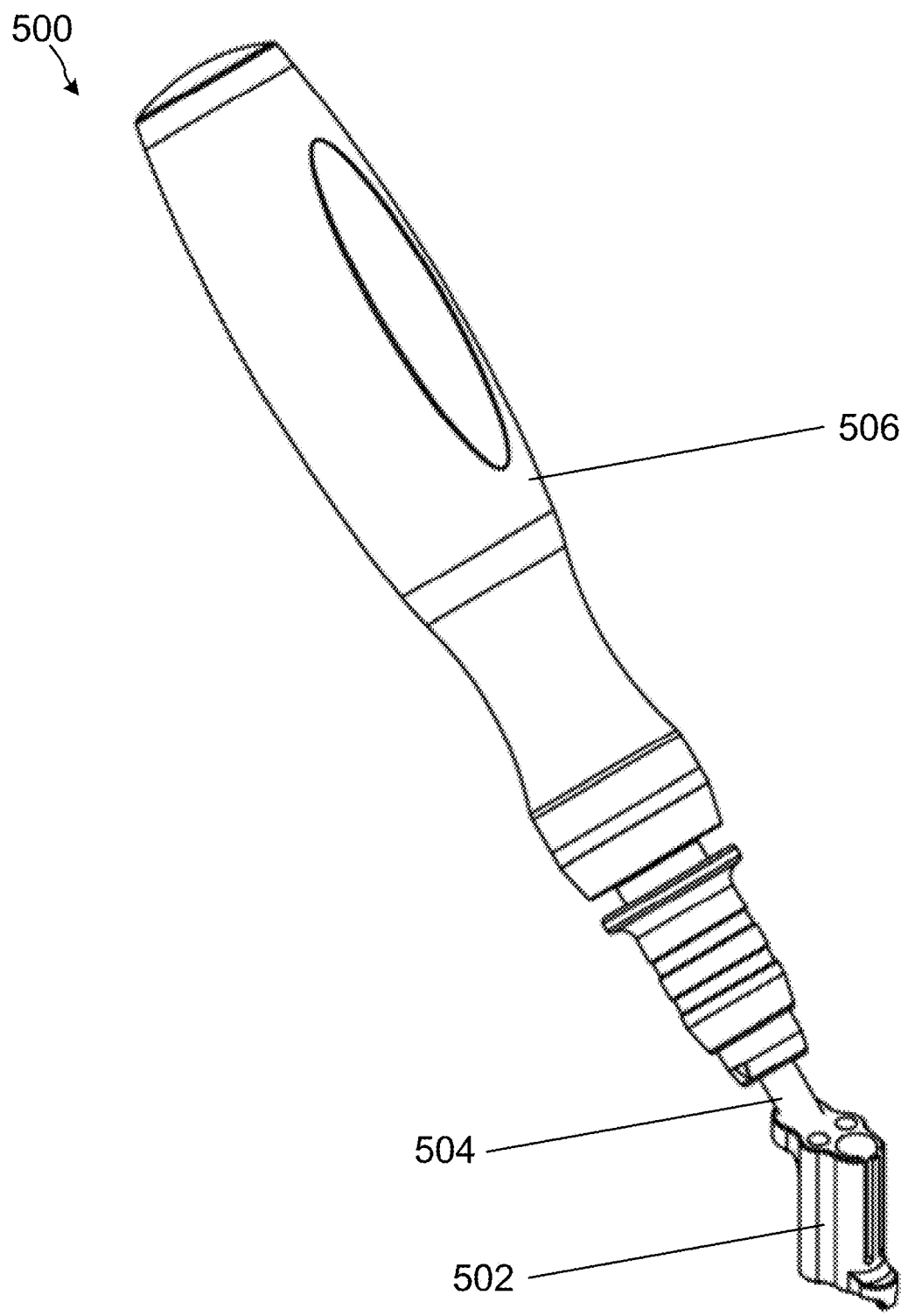
FIGS. 20A-20C illustrate perspective views of an implant positioning device in accordance with an embodiment of the disclosure.
Figure 20B:
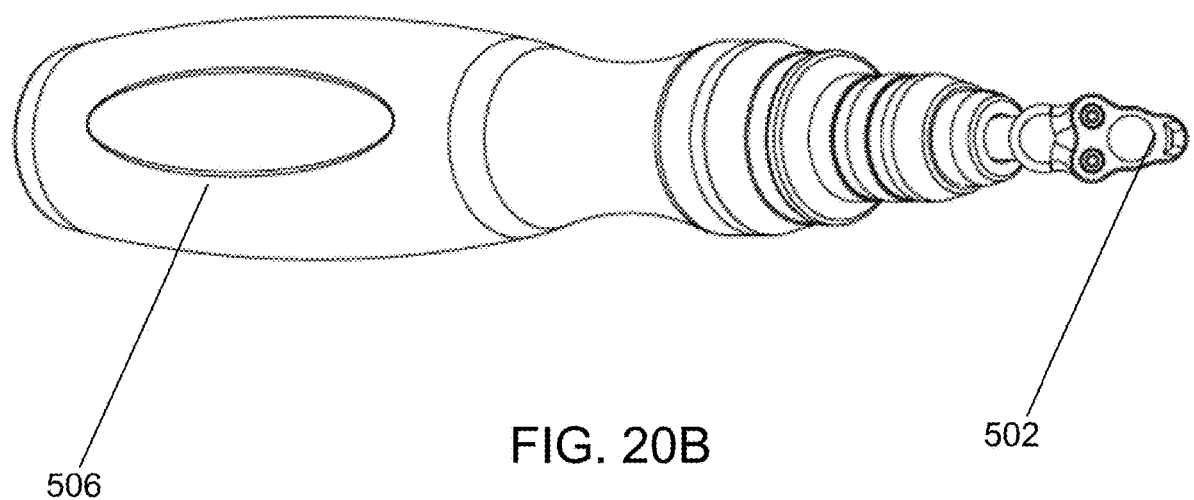
Figure 20C:
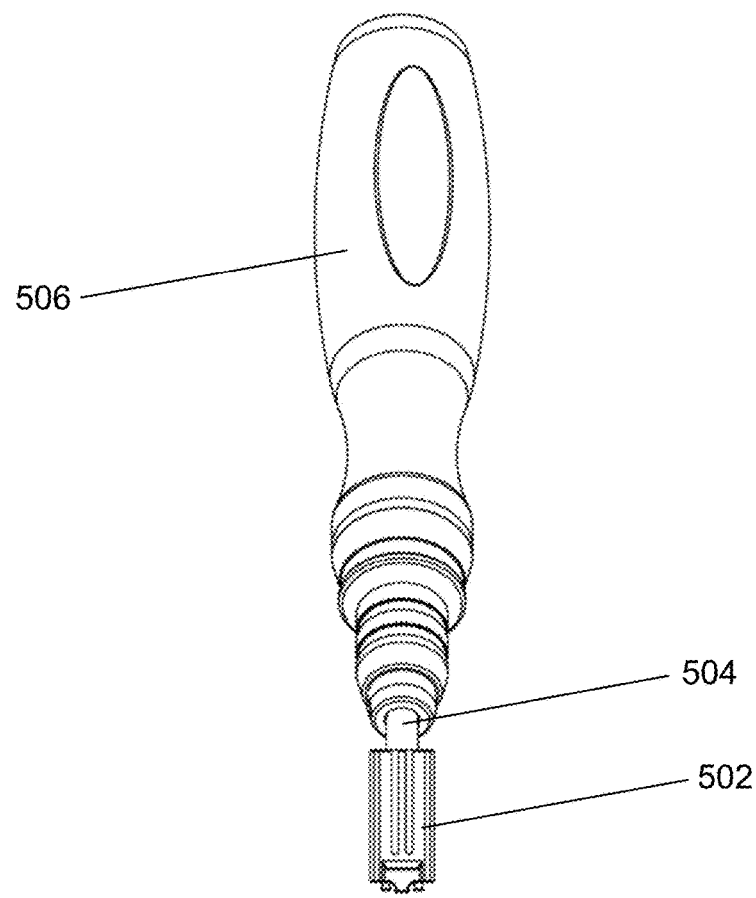

FIGS. 17-19 illustrate a collar 314 that may be coupled to the fastener guide 300 when the fastener guide 300 is coupled to the plate 400. The collar 314 may be configured to slide over a distal or proximal end of the fastener guide 300 and securely fit around the body 302 of the fastener guide 300 to minimize movement or flexing of the attachment arms 308 away from one another. This minimizes the risk of the fastener guide 300 being accidentally decoupled from the plate 400.

Additionally, the collar 314 may include fixed or retractable protrusions 316. The protrusions may be disposed on an inner part of the collar 316 and on opposite sides of the collar 314, such that the protrusions 316 align with and contact the attachment arms 308. When the protrusions 316 are fixed, the collar 314 may be disposed on the fastener guide 300 by moving or flexing the attachment arms 308 towards one another and sliding the collar 314 onto the distal end of the fastener guide 300, with the protrusions 316 aligned with the attachment arms 308. When the end of the collar 314 clears the ends of the attachment arms 308, the attachment arms 308 may move or spring back away from one another. The protrusions 316 extend and fit into the lower grooves of the body 302 to minimize movement or flexing of the attachment arms 308 away from one another. This also minimizes the risk of the collar 314 falling off of or being accidentally removed from the body 302. For example, once the collar 314 is disposed on the body 302, the collar 314 may be moved or slid upward towards the proximal end of the body 302 (i.e., the protrusions 316 may be slid within the lower grooves of the body 302) to allow the attachment arms 308 to move or flex away from each other and allow the fastener guide 300 to be coupled to the plate 400. When the fastener guide 300 is coupled to the plate 400, the collar 314 may be moved downward towards the distal end of the body 302 to cause the protrusions 316 to contact the guide arms 308 and restrict movement of the attachment arms 308 away from one another and the fastener guide 300 from being accidentally decoupled from the plate 400.

In another aspect, the protrusions 316 may be configured to flex or retract when the collar 314 is slid over the proximal end of the fastener guide 300 to allow the collar 314 to fit over the proximal end of the body 302. When the collar 314 is slid towards the distal end of the body 302, the protrusions 316 may be configured to extend and fit into the lower grooves of the body 302 to minimize movement or flexing of the attachment arms 308 away from one another. For example, when the protrusions 316 are retractable the protrusions 316 may be a spring loaded button that retracts when pressure is applied to the button and extends back inward towards a middle of the collar 314 when the pressure is removed.

FIGS. 20A-25 illustrate a fastener guide 500 for use with an implant positioning device according to an embodiment of the disclosure. The fastener guide 500 may have fastener guide portion 502 and a handle extension portion 504 adapted to couple to a handle 506. The fastener guide portion 502 may be adapted to receive and align a fastener for use with the implant positioning device. The handle extension portion 504 (also referred to as a coupling extension or portion) is coupled to the fastener guide portion 502 and extends away from the fastener guide portion. Further, the handle extension portion 504 may be adapted to receive and removably couple to a handle 506.

Figure 21A:
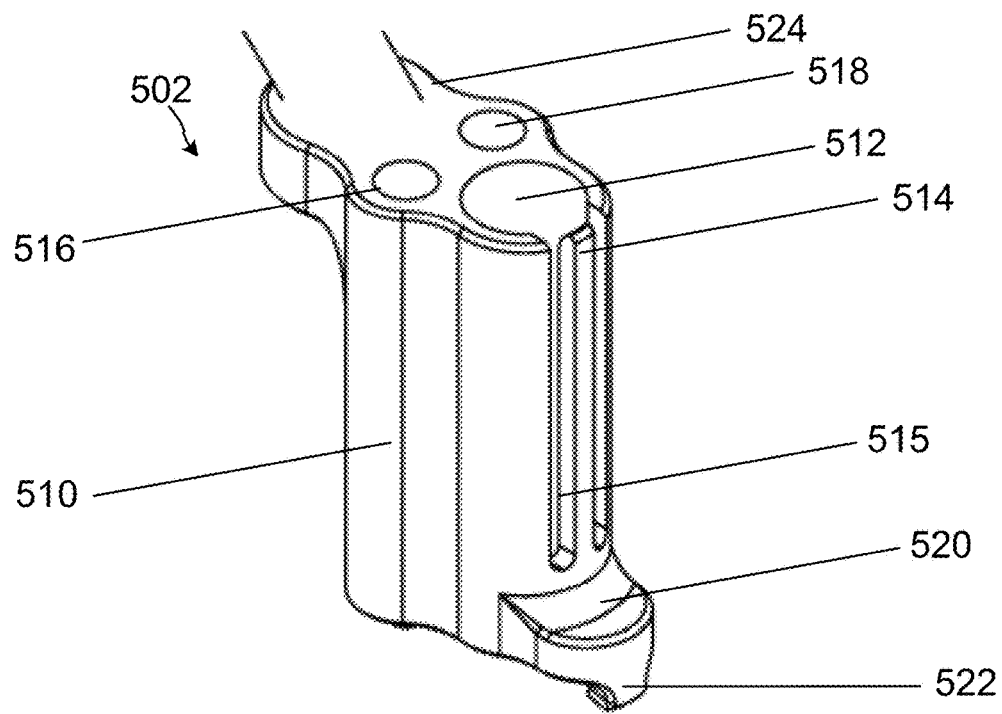
FIGS. 21A-21B illustrate enlarged perspective views of the fastener guide of the implant positioning device of FIG. 20 in accordance with an embodiment of the disclosure.
Figure 21B:
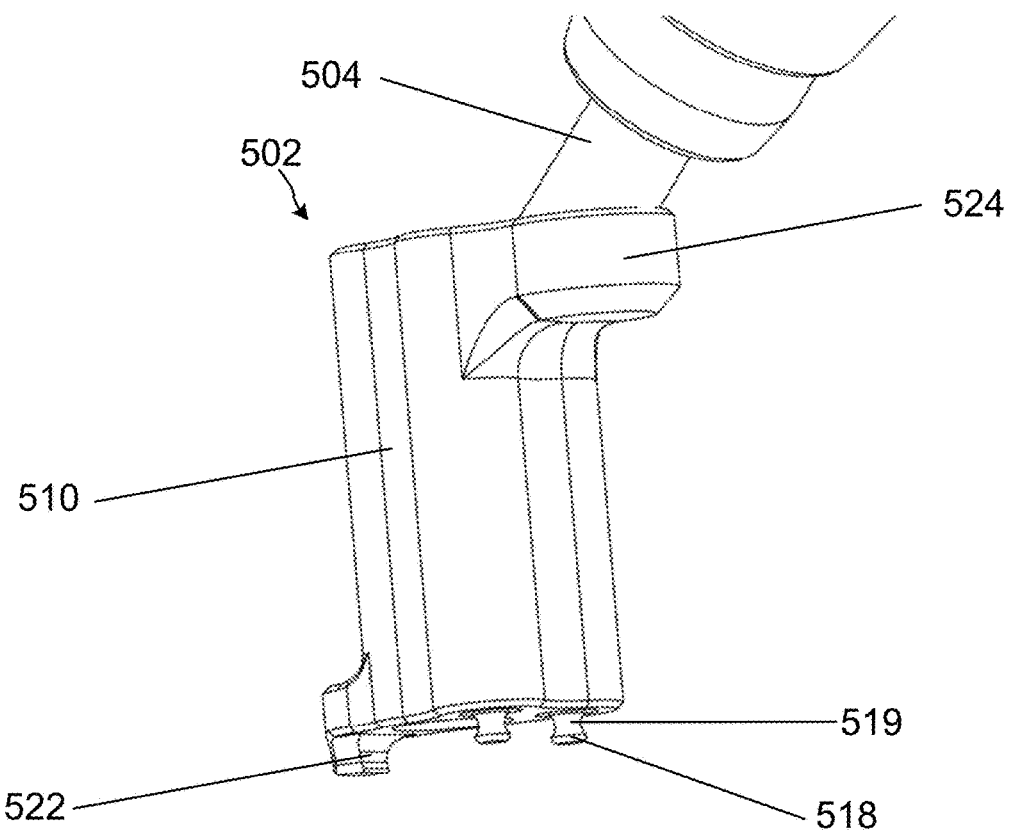

As illustrated in FIGS. 21A and 21B, the fastener guide portion 502 includes a frame or a body portion 510. The body portion 510 includes a fastener aperture 512 adapted to receive a fastener and a guide arm 514 (which may be a finger-like structure) formed on a first end or proximal end of the fastener guide portion 502 by slits or apertures 515 that extend in a longitudinal direction of the body portion 510. The guide arm 514 may extend into an inner diameter of the fastener aperture 512 proximal to the first end of the fastener guide portion 502. The guide arm 514 is adapted to releasably hold, guide, and position a fastener that may be used to couple an orthopaedic fixation device, such as a plate, to a bone or other body part. The proximal end of the fastener guide portion 502 also allows a top of the fastener to be exposed. This allows access for a fastener driver to access and engage a head of the fastener. The fastener may be a screw, pin, rivet, and other type of fastener, etc., and the guide arm 514 may serve as an expansion zone to help capture a wide variety of fasteners effectively.

In this embodiment, the slits 515 may be disposed on opposite sides of the guide arm 514. By having the slits 515 disposed on opposite sides of the guide arm 514, the guide arm 514 is allowed to elastically move or flex away from the body 510 to allow the fastener to be moved or pushed through the fastener aperture 512, when the fastener is driven into a bone or other body part. Additionally, the guide arm 514 and the slits 515 may be disposed on the body 510 such that the guide arm 514 forms part of an outer portion of the body 510.

The body portion 510 may also have one or more channels or cannulas 516 at the first/proximal end of the fastener guide portion 502. In one aspect, the cannulas 516 may be spaced apart by about 60 degrees. Each cannula 516 is adapted to receive a retaining beam 518. The retaining beam 518 may be inserted into the cannulas 516 and retained within the cannulas 516 by press-fit within the cannula 516. Further, the retaining beam 518 may be welded, coupled with adhesive, or other retaining method in the cannula 516. For example, the retaining beam 518 may be welded at the first/proximal end of the body 510 to ensure the retaining beam 518 remains within the cannula 516. However, the retaining beams 518 may also be inserted into the cannula 516 using a number of different methods. For example, the retaining beams 518 may be screwed into the cannula 516 using threads that are formed on the proximal end of the retaining beam 518 and cannula 516.

The retaining beams 518 are adapted to removably couple the fastener guide 400 to a plate, such that the fastener guide 500, or fastener disposed within fastener guide 500, is in alignment with a fastener aperture in the plate. While two retaining beam 518 are illustrated, the fastener guide 500 may have additional retaining beams 518 as needed, to removably couple the fastener guide 500 with the plate.

Each retaining beam 518 has a first or proximal end that is substantially the same size as a diameter of the cannula 516 to allow the retaining beam 518 to be press-fit into the cannula 516. The retaining beam 518 also has a second or distal end that is opposite the first/proximal end that has a diameter less than the diameter of the first end. The smaller second end of the retaining beam 518 allows the retaining beam to flex within the cannula 516 to removably couple with a plate. In addition, the cannula 516 may restrict the retaining beam 518 from becoming deformed due to over flexing.

Further, the second end has a retaining channel 519 formed around the retaining beam 518 to receive a side of a plate. The retaining channel 519 may be shaped to reflect a shape of the side of the plate to be received to removably couple the fastener guide to the plate, as shown in FIGS. 22-24B.

The fastener guide portion 502 may also include rails 520 that extend from the second/distal side of the body 510 proximal to an outer portion of the body 510 opposite from the handle extension portion 504. The rails 520 may be used to couple and restrict a plate from spinning and/or angular or rotational movement of the plate when removably coupled to the implant fixation device 500. In addition, each rail 520 may also have a rail foot 522 to receive an edge of a plate to be removably coupled to the implant fixation device 500 and further limit movement of a plate that is attached to the implant fixation device 500.

In addition, the body 510 may also have handle rail 524 that extends from a proximal side of the body 510. The handle rail 524 is adapted to receive and couple the handle extension portion 504 to the fastener guide portion 502.

Figure 22:
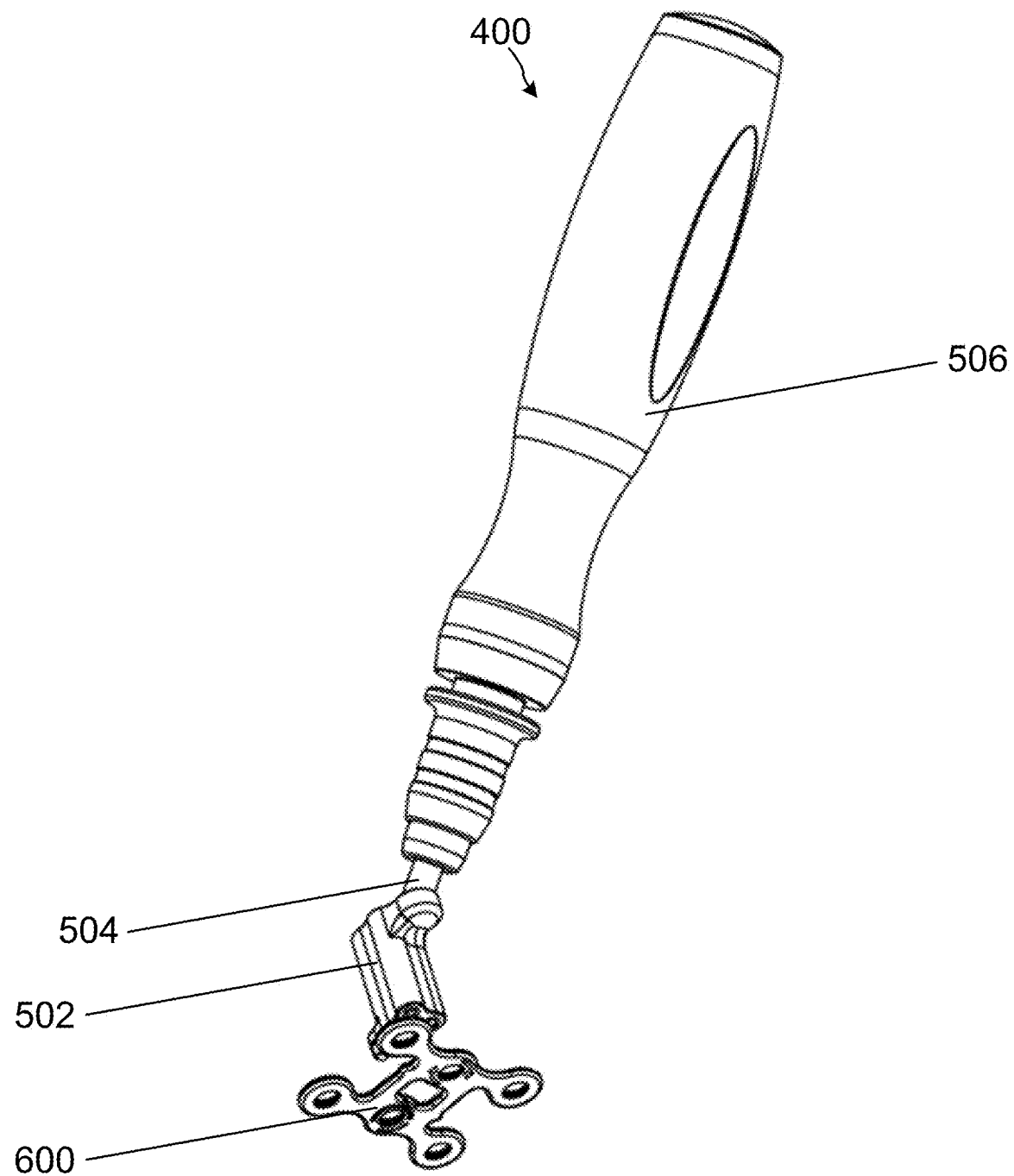
FIG. 22 illustrates a perspective view of the implant positioning device of FIG. 20 aligned with a plate in accordance with an embodiment of the disclosure.
Figure 23A:
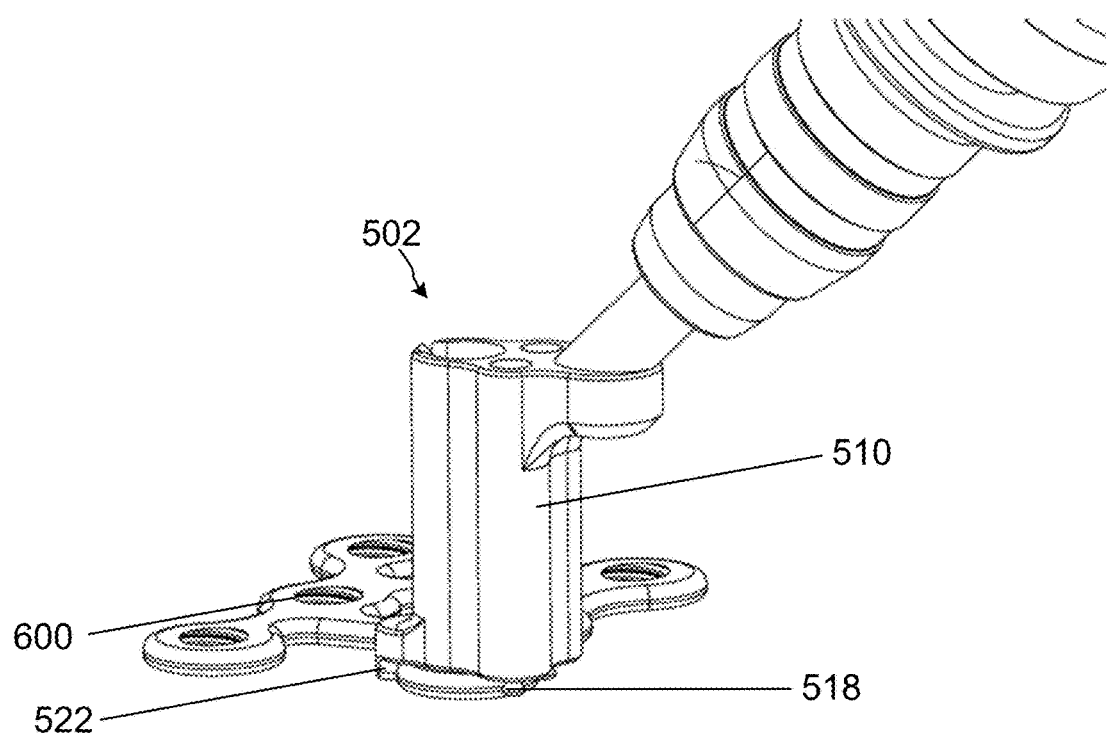
FIGS. 23A-23B illustrate enlarged perspective views of the implant positioning device of FIG. 20 aligned with a plate in accordance with an embodiment of the disclosure.
Figure 23B:
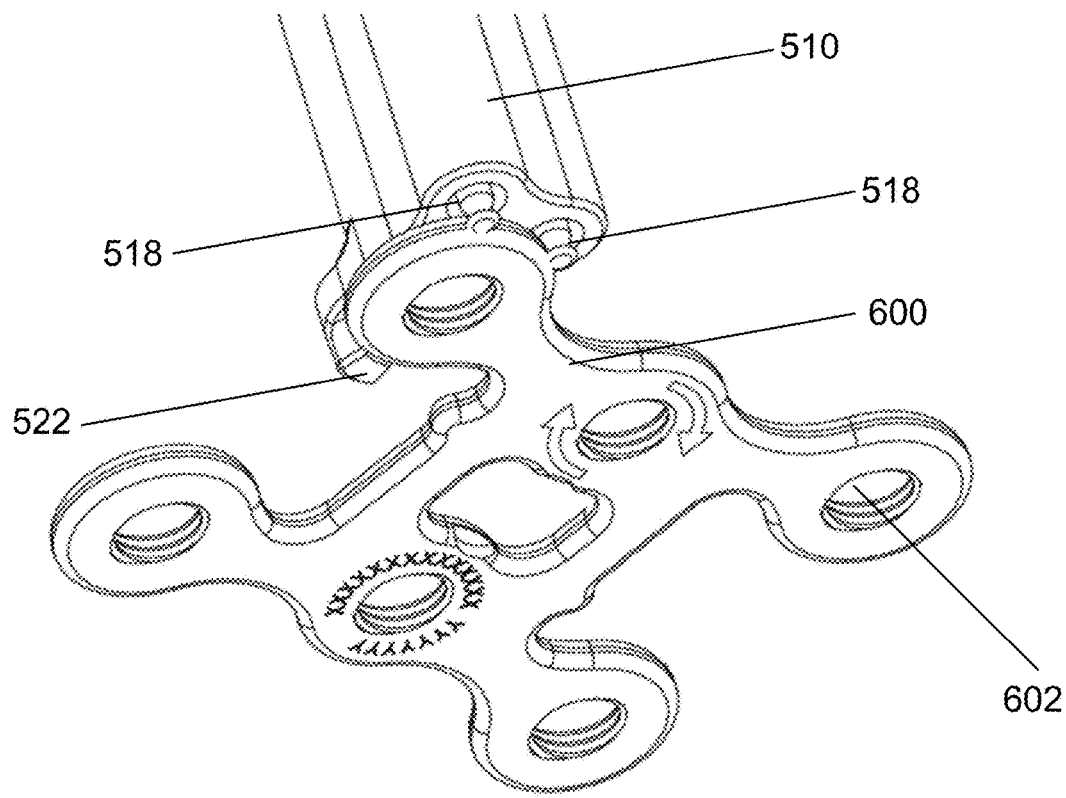

FIGS. 22-23B illustrate the implant positioning device 500 removably coupled to and aligned with a plate 600. As illustrated in FIGS. 23A and 23B, the outer portion of plate 600 that surrounds each plate fastener aperture 602 may be adapted to receive the retaining beams 514 of the fastener guide 502 to removably couple the fastener guide 502 to the plate 600. Further, the outer portion of the plate 600 may also couple to the rail foot 522 of the fastener guide 502 to removably couple to the fastener guide 502 and further limit movement of the plate 600 while attached to the fastener guide 502.

Figure 24A:
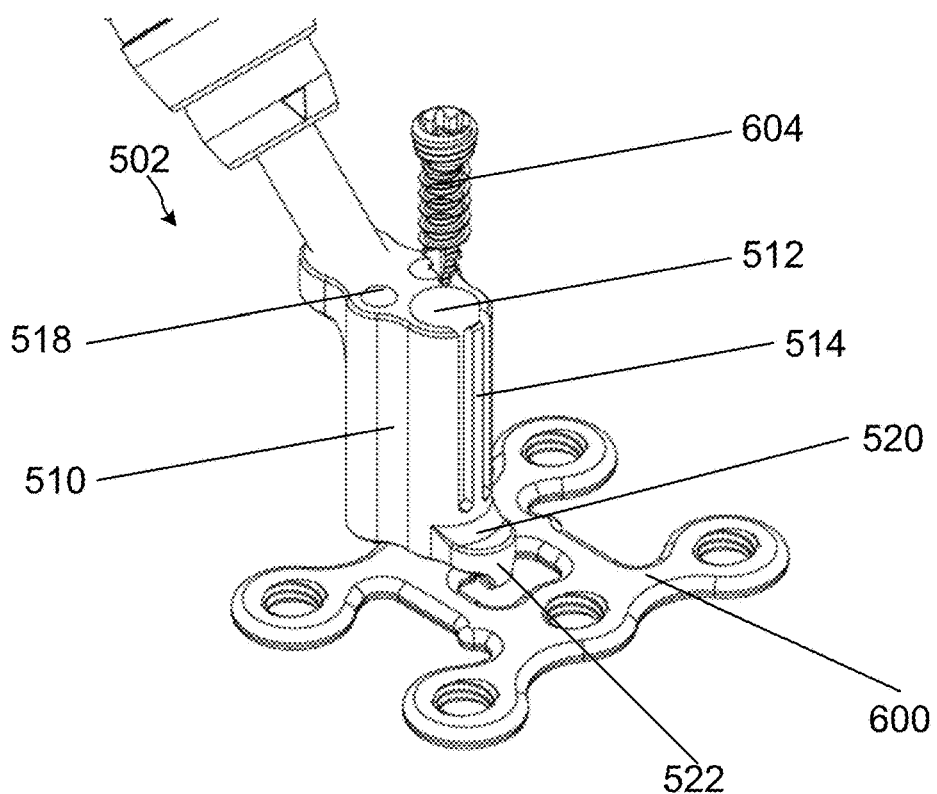
FIGS. 24A-24B illustrate enlarged perspective views of the implant positioning device of FIG. 20 aligned with a plate and receiving a fastener in accordance with an embodiment of the disclosure.
Figure 24B:
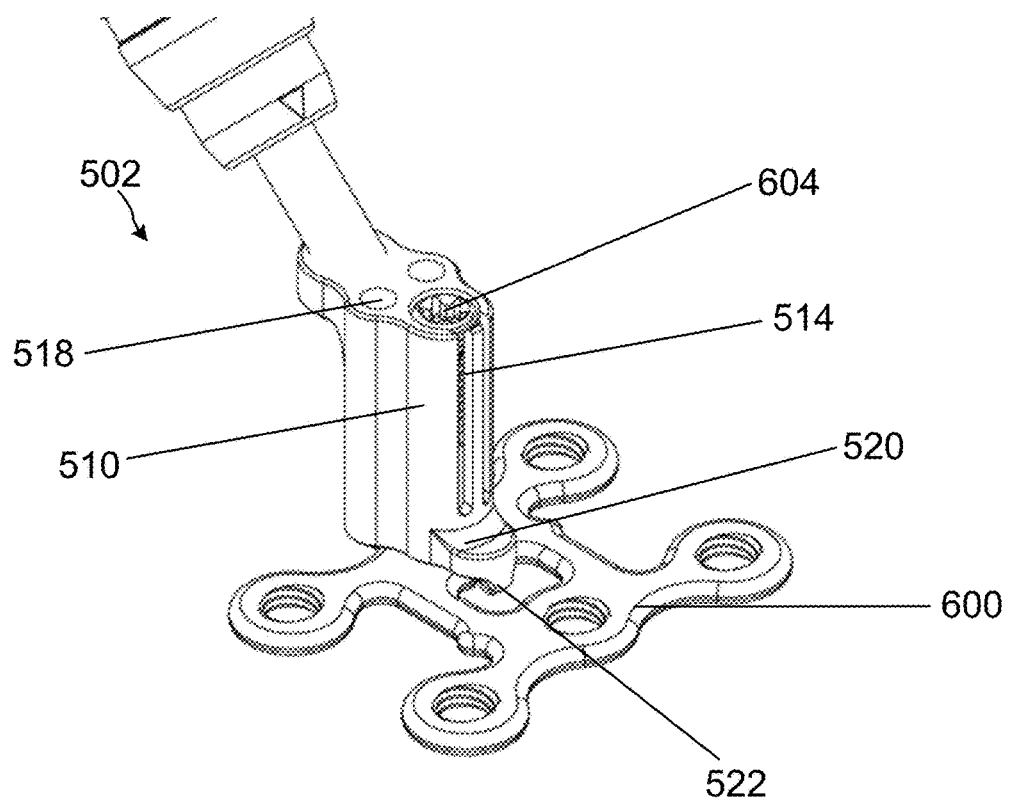

FIGS. 24A and 24B illustrate the fastener guide portion 502 receiving a fastener 604 and the fastener guide portion 502 is aligned with a plate 600 in accordance with an embodiment of the disclosure. As described above, the fastener aperture 512 receives the fastener 604. The guide arm 514 may be used to releasably hold, guide, and position a fastener that may be used to couple an orthopaedic fixation device, such as a plate, to a bone or other body part. Further, the slits 515 that may be disposed on opposite sides of the guide arm 514 allow the guide arm 514 to elastically move or flex away from the body 510 to allow the fastener 604 to be moved or pushed through the fastener aperture 512, when the fastener 604 is driven into a bone or other body part.

In one example, the fastener guide 502 may be preloaded with a fastener by placing the fastener 604 in the first end of the fastener guide portion 502. This may include pushing the fastener 604 into the fastener aperture 512 until a head of the fastener 604 is gripped and held in place by the guide arm 514. The fastener guide 502 may then be coupled to a plate, such as plate 600, by pushing the retaining beams 518 onto the plate 600. This may cause the retaining beams 518 to move or flex away from the body 510, and then snap towards the body 510 on the side of the plate 600 once past the plate 600. It should be appreciated that the implant fixation device 500 may be coupled to a plate, such as plate 600, prior to the insertion of the fastener.

Figure 25A:
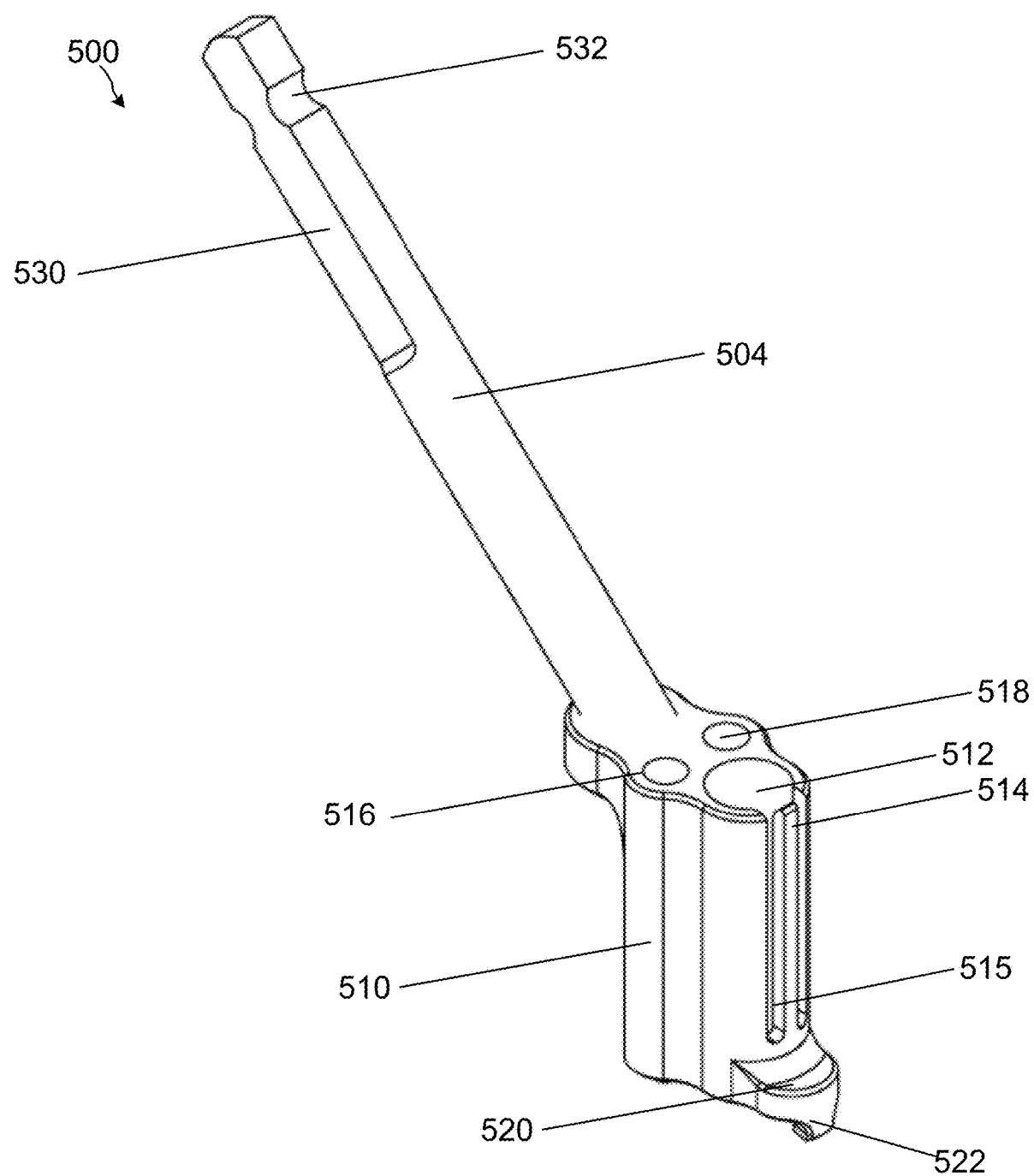
FIGS. 25A-25C illustrate perspective views of the implant positioning device of FIG. 20 removed from a handle in accordance with an embodiment of the disclosure.
Figure 25B:
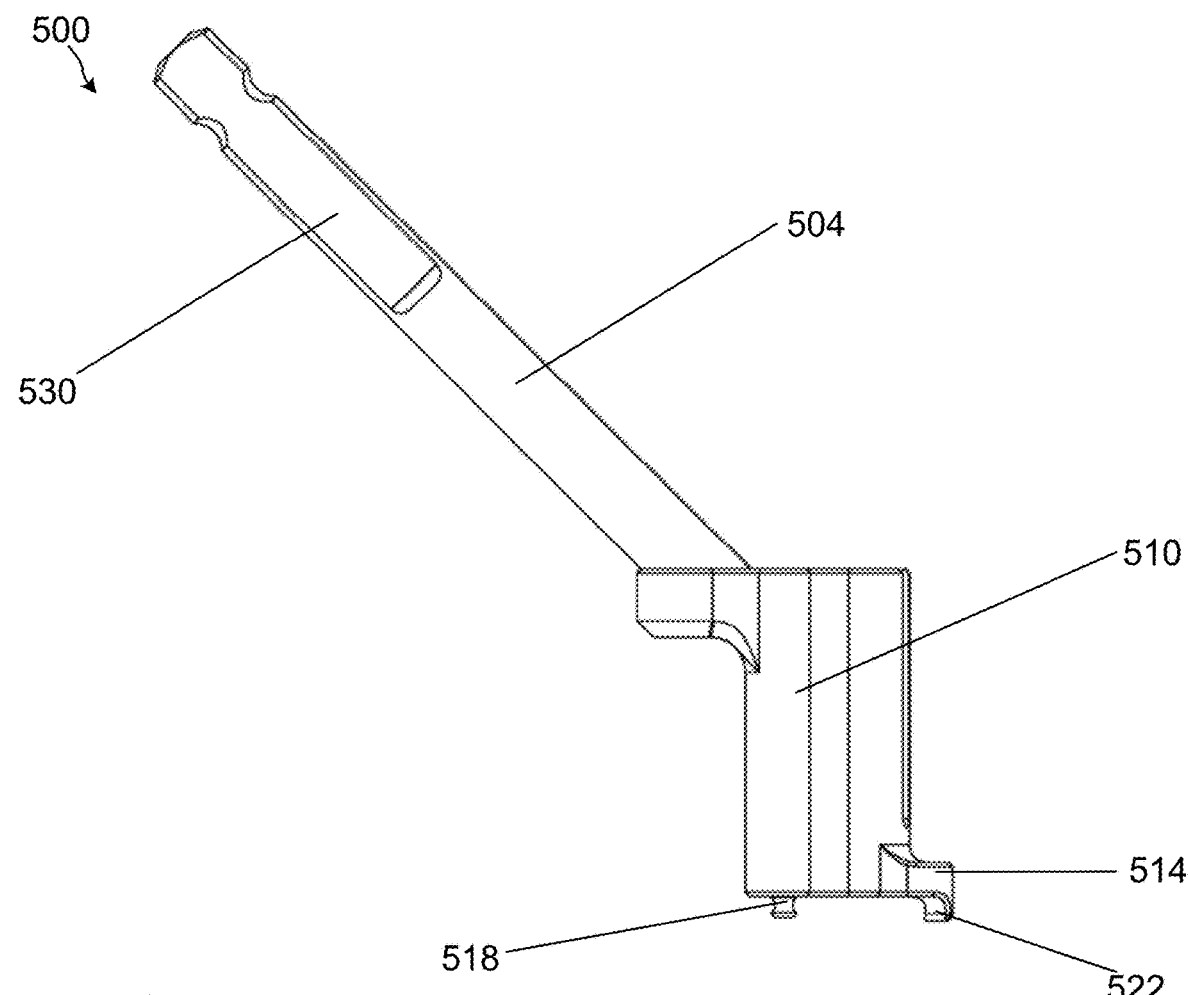
Figure 25C:
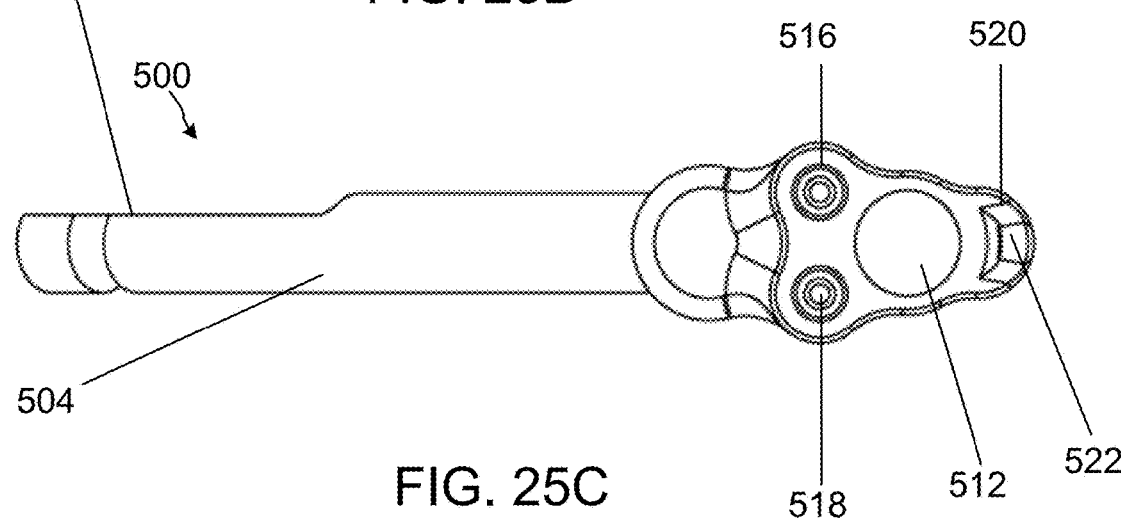

As illustrated in FIGS. 25A-25C, the handle extension portion 504 may include a handle coupling portion 530. The handle coupling portion 530 may be adapted to receive and removably couple a handle, such as handle 506, to the fastener guide 500. Additionally, the handle coupling portion 530 may also include a handle coupling indent 532 adapted to further limit slipping and/or rotation of the handle when coupled to the fastener guide 500.

FIGS. 26-33 illustrate a fastener guide 700 for use with an implant positioning device according to an embodiment of the disclosure. The fastener guide 700 may have fastener guide portion 702 and a handle extension portion 704. The fastener guide portion 702 may be adapted to receive and align a fastener for use with the implant positioning device. The handle extension portion 704 is coupled to the fastener guide portion 702 and extends away from the fastener guide portion 702. Further, the handle extension portion 702 may be adapted to receive and removably couple to a handle, such as handle 506.

Figure 26:
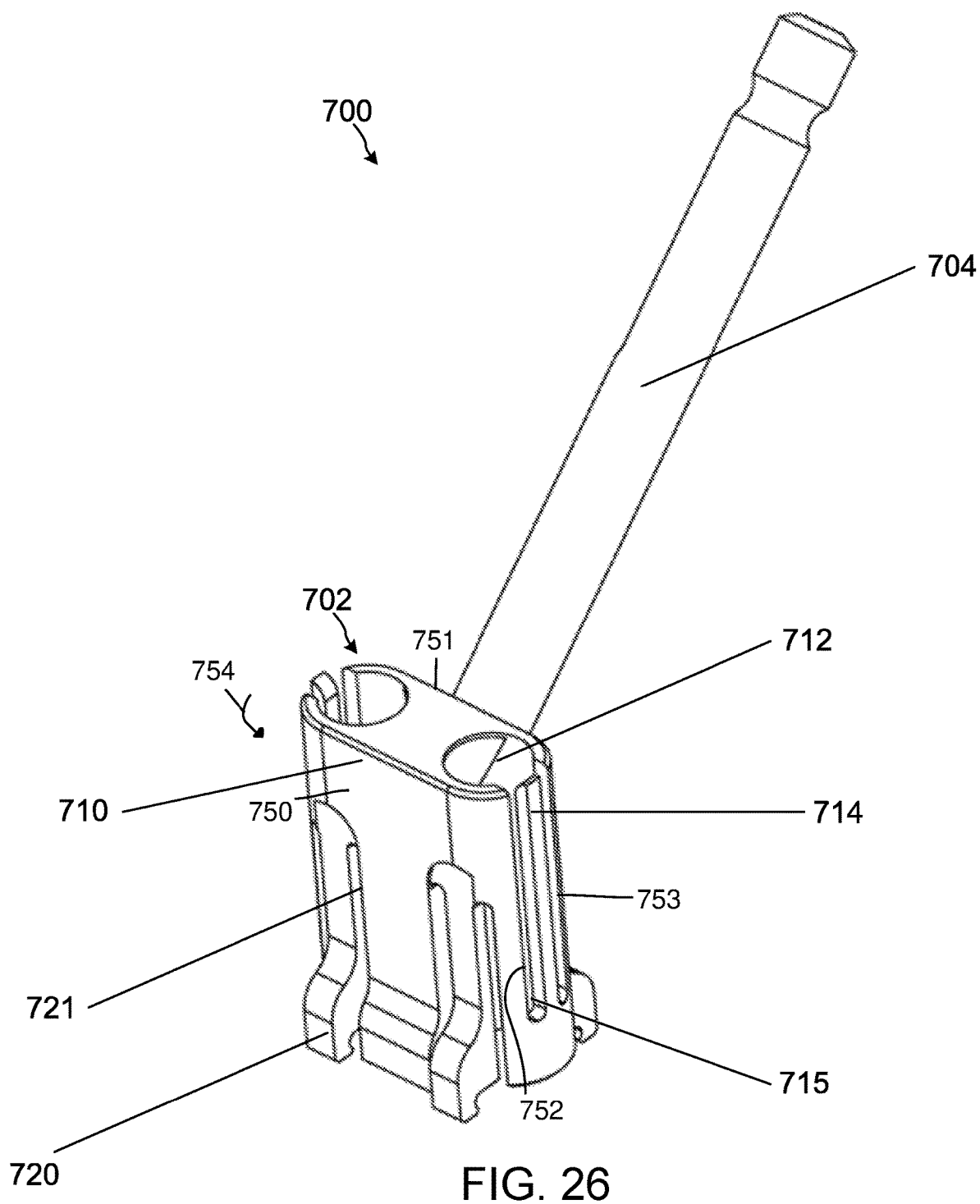
FIG. 26 illustrates a perspective view of an implant positioning device in accordance with an embodiment of the disclosure.
Figure 27:
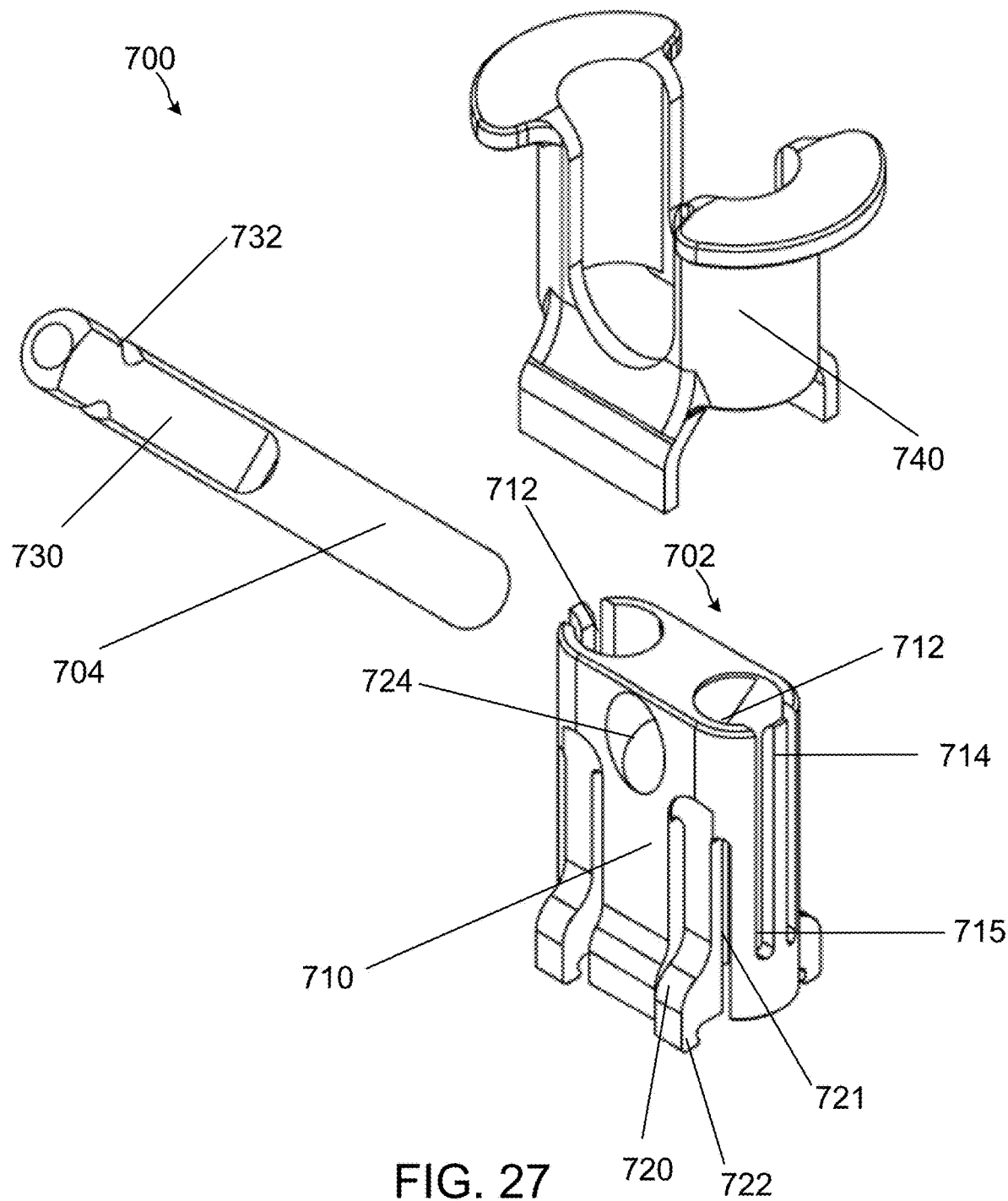
FIG. 27 illustrates an exploded perspective view of the implant positioning device of FIG. 26 with a collar in accordance with an embodiment of the disclosure.

As illustrated in FIGS. 26 and 27, the fastener guide portion 702 includes a frame or a body portion 710. The body portion 710 includes more than one fastener apertures 712, each adapted to receive a fastener and each fastener aperture 712 includes a guide arm 714 (which may be a finger-like structure) formed on a first end or proximal end of the fastener guide portion 702 by slits or apertures 715. The guide arm 714 may extend into an inner diameter of the fastener aperture 712 proximal to the first end of the fastener guide portion 702. The guide arm 714 is adapted to releasably hold, guide, and position a fastener within the respective fastener aperture 712, in which the fastener may be used to couple an orthopaedic fixation device, such as a plate, to a bone or other body part. The proximal end of the fastener guide portion 702 also allows a top of the fastener to be exposed. This allows for a fastener driver to access and engage a head of the fastener. The fastener may be a screw, pin, rivet, and/or other type of fastener, etc., and each guide arm 714 may serve as an expansion zone to help capture a wide variety of fasteners effectively within the fastener aperture 714.

In this embodiment, the slits 715 may be disposed on opposite sides of each guide arum 714, and extend in a longitudinal direction of the body portion 710. By having the slits 715 disposed on opposite sides of the guide arm 714, the guide arm 714 is allowed to elastically move or flex away from the body 710 to allow the fastener to be moved or pushed through the fastener aperture 712, when the fastener is driven into a bone or other body part. Additionally, the guide arm 714 and the slits 715 may be disposed on the body 710 such that the guide arm 714 forms part of an outer portion of the body 710. Further, the body 710 includes a first portion 750 and a second portion 751, and the slits 715 include a first slit 752 and a second slit 753. In a circumferential direction 754 of the fastener guide portion 702 at the first end of the body 710, the fastener guide portion 702 includes the first portion 750 of the body 710, the first slit 752 of the slits 715, the guide arm 714, the second slit 753 of the slits 715, and the second portion 751 of the body 710.

The body 710 may also include a pair of coupling legs 720 disposed adjacent to each fastener aperture 712 formed on a second end or distal end of the fastener guide portion 702 by slits or apertures 721. In this embodiment, the slits 721 may be disposed on opposite sides of each coupling leg 720. By having the slits 721 disposed on opposite sides of the coupling leg 720, the coupling leg 720 is allowed to elastically move or flex away from the body 710 to allow the fastener guide 700 to be moved or pushed onto a plate to removably couple the plate to the fastener guide 700 and limit movement of the plate once removably coupled to the fastener guide 700. Additionally, the coupling leg 720 may extend from an outer portion of the body 710 such that the guide leg 720 extends past the outer portion of the body 710. In addition, each coupling leg 720 may have a coupling foot 722 adapted to receive an edge of a plate to be removably coupled to the fastener guide 700 and further limit movement of a plate that is coupled to the fastener guide 700.

Further, the body 710 may have a handle aperture 724 formed in a middle portion of the body 710. The handle aperture 724 is adapted to receive and couple the handle extension portion 704 to the fastener guide portion 702. While the handle aperture 724 is shown formed in a middle portion of the body 710, the handle aperture 724 may be formed anywhere on the body 710 to allow the handle extension portion 704 to be coupled to the fastener guide portion 702.

The handle extension portion 704 may include a handle coupling portion 730 adapted to receive and removably couple a handle, such as handle 506, to the fastener guide 700. Additionally, the handle coupling portion 730 may include a handle coupling indent 732 adapted to further limit slipping and/or rotation of the handle when coupled to the fastener guide 700.

Figure 28:
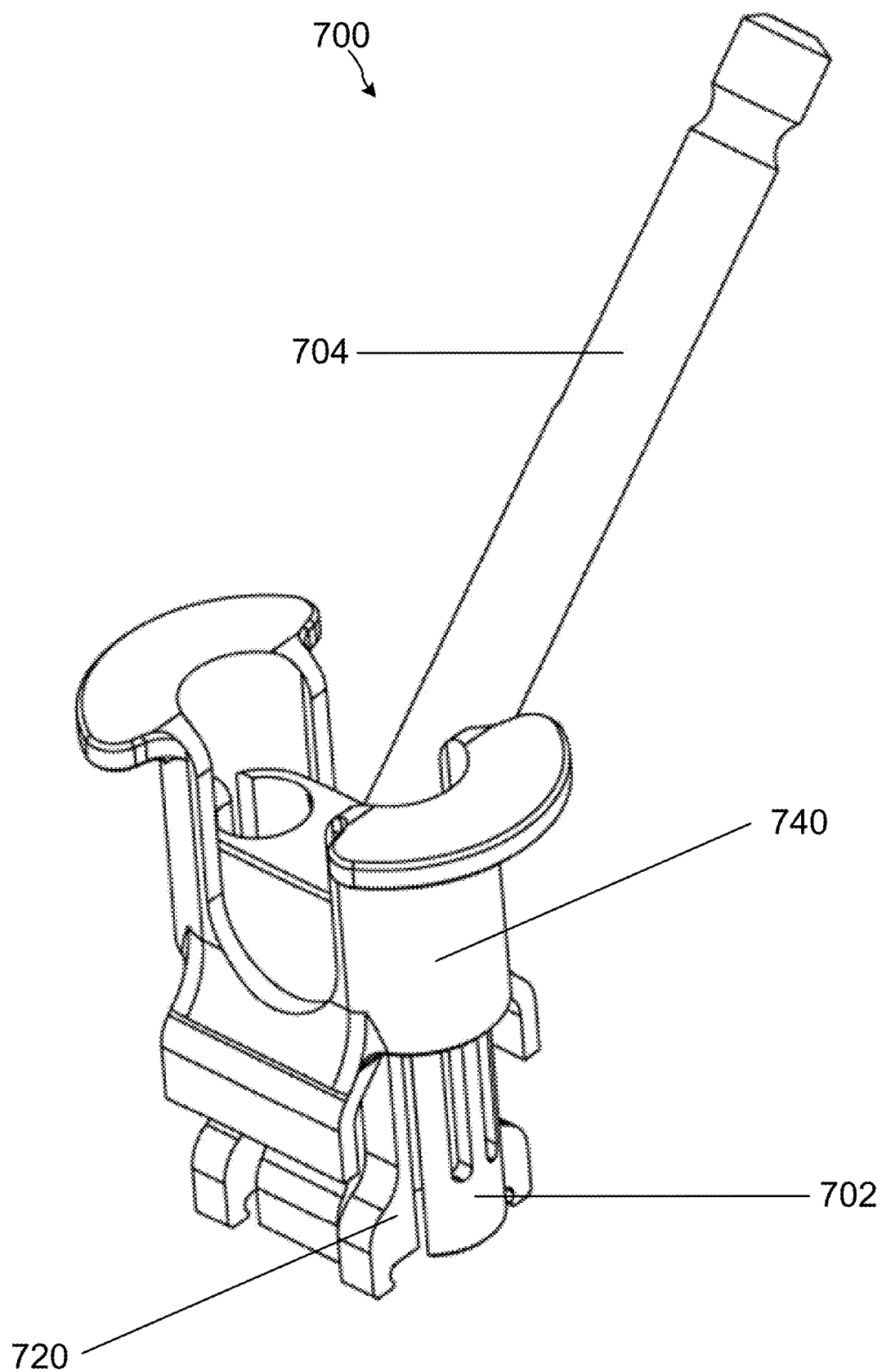
FIG. 28 illustrates a first perspective view of the implant positioning device of FIG. 26 aligned with the collar in accordance with an embodiment of the disclosure.
Figure 29:
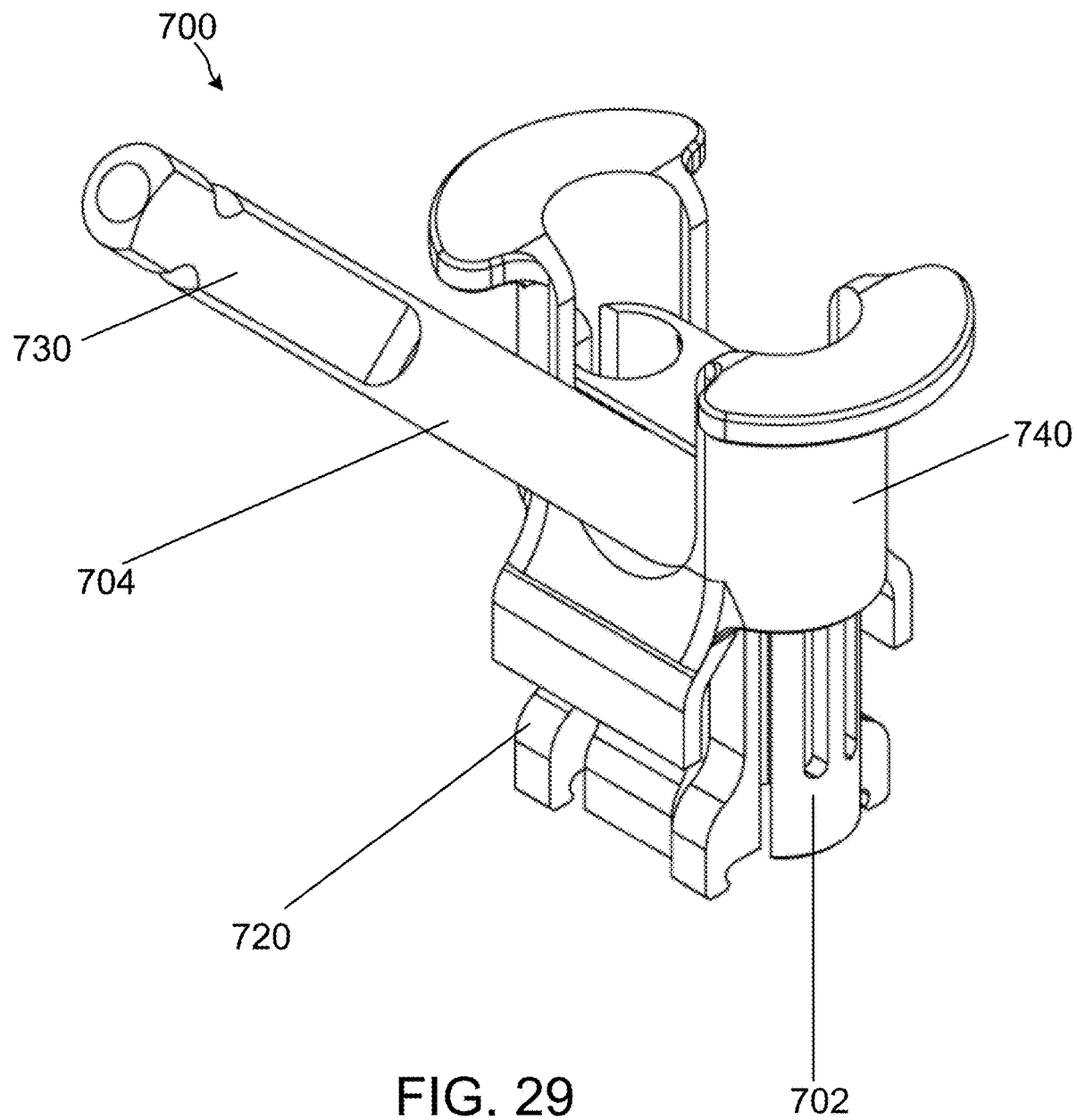
FIG. 29 illustrates a second perspective view of the implant positioning device of FIG. 26 aligned with the collar in accordance with an embodiment of the disclosure.
Figure 30:
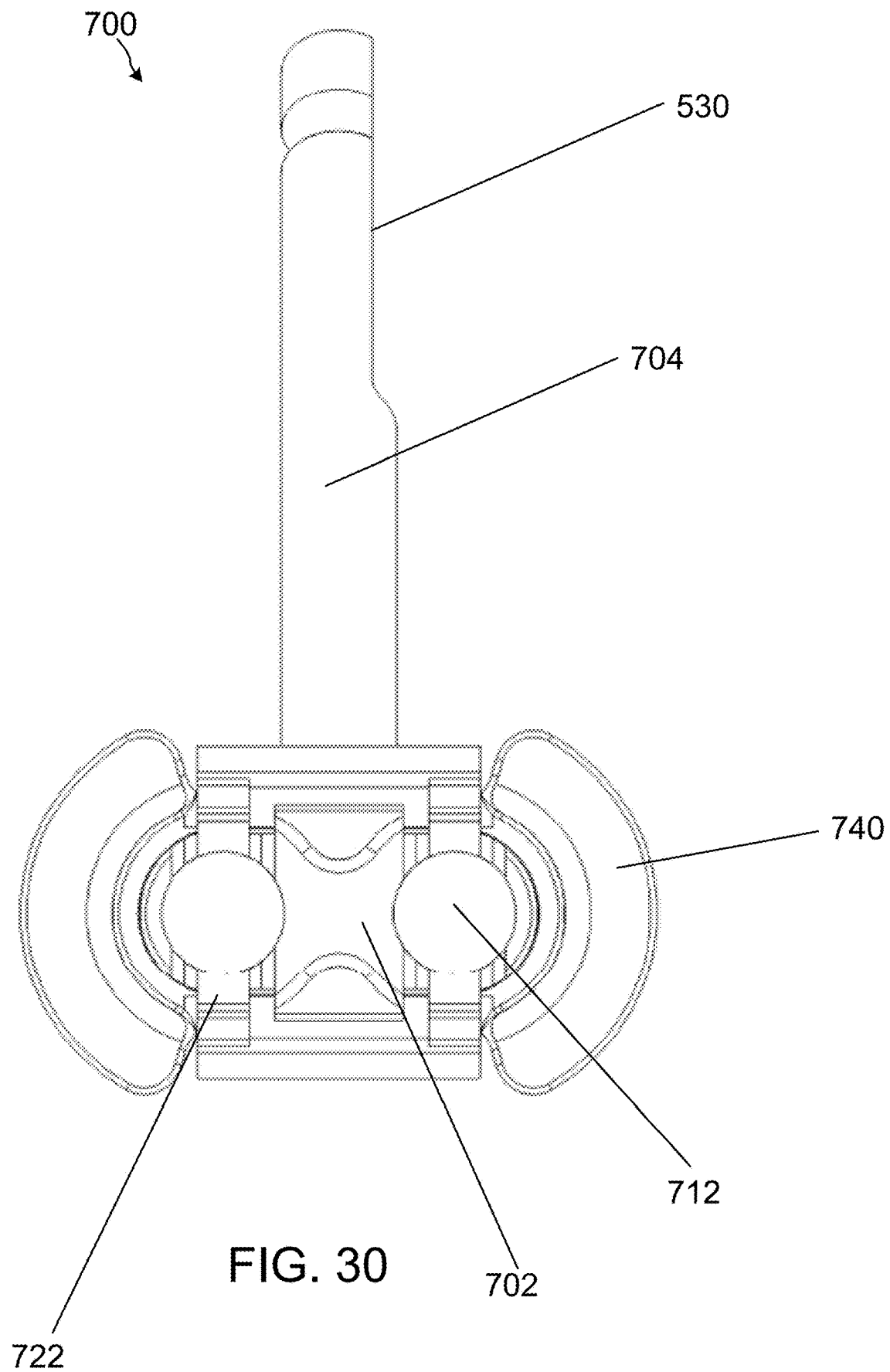
FIG. 30 illustrates a third perspective view of the implant positioning device of FIG. 26 aligned with the collar in accordance with an embodiment of the disclosure.
Figure 31:
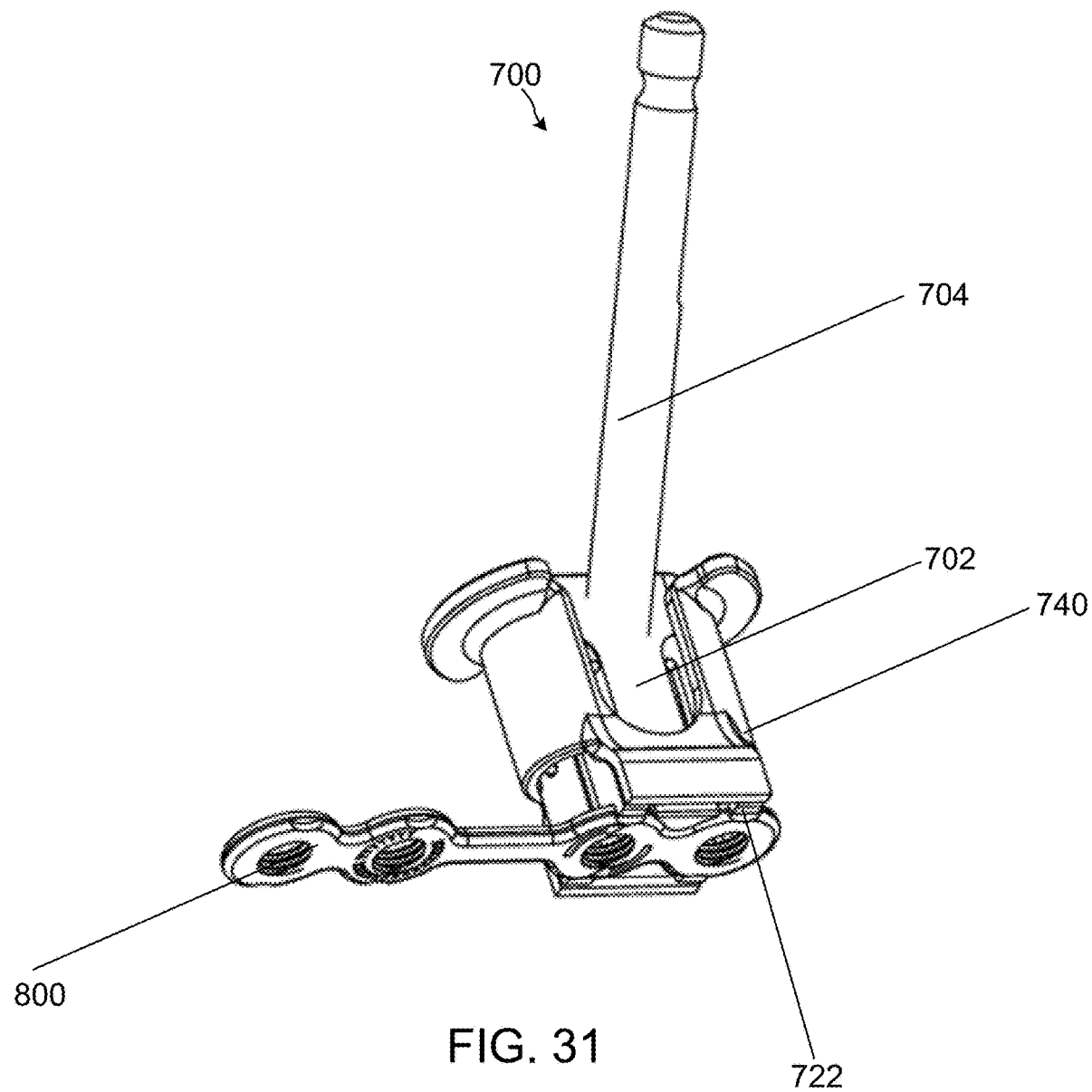
FIG. 31 illustrates a first perspective view of the implant positioning device of FIG. 26 aligned with a plate and the collar in accordance with an embodiment of the disclosure.

The fastener guide 700 may also include a fastener guide collar 740. The fastener guide collar 740 may be disposed around an exterior of the fastener guide portion 702. The fastener guide collar 740 can also be positioned in an up (disengaged) and a down (engaged) position. When in the up (disengaged) position as shown in FIGS. 28 and 29, the fastener guide collar 740 allows the coupling leg 720 to elastically move or flex away from the body 710 to allow the fastener guide 700 to be moved or pushed onto a plate. When in the down (engaged) position as shown in FIGS. 30-33, the fastener guide collar 740 restricts the coupling leg 720 from elastically moving or flexing away from the body 710 to restrict the fastener guide 700 from uncoupling from a plate 800.

Figure 32A:
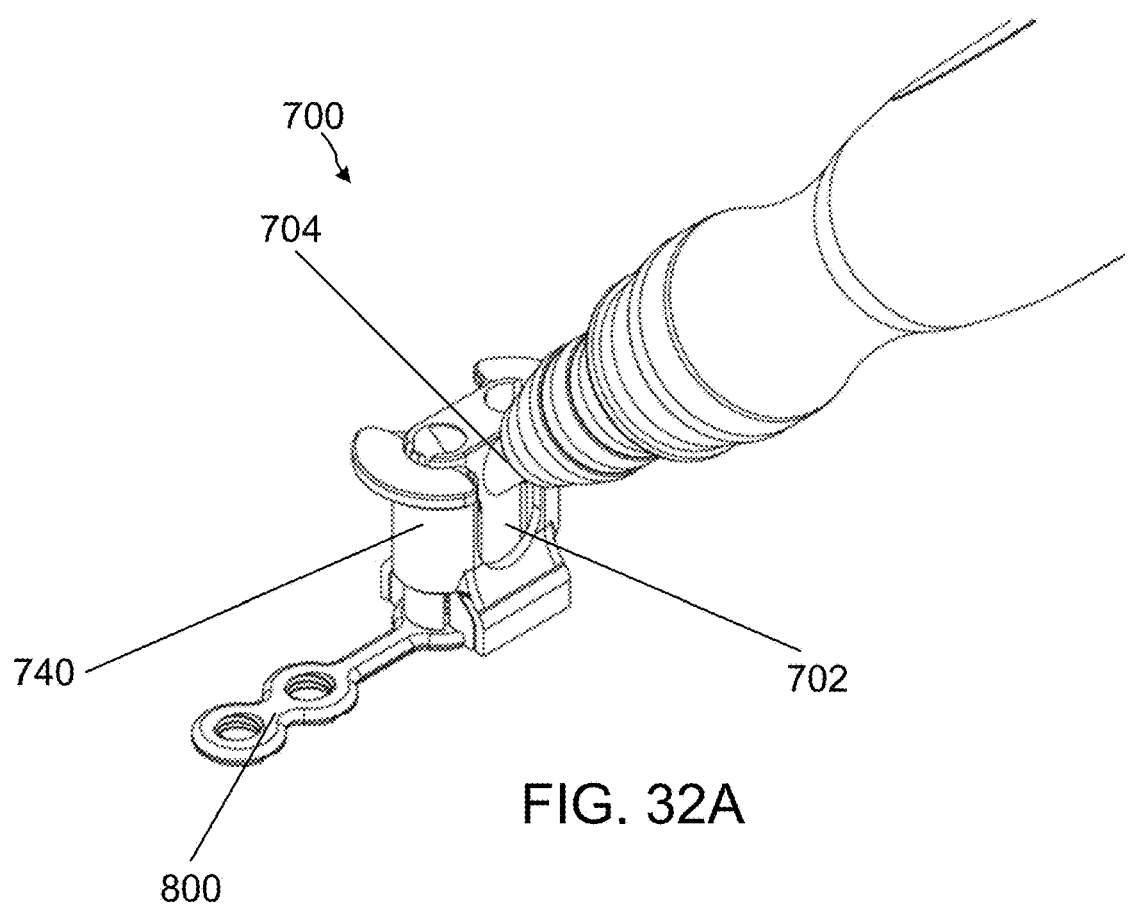
FIGS. 32A-32B illustrate perspective views of the implant positioning device of FIG. 26 aligned with a plate and the collar in accordance with an embodiment of the disclosure.
Figure 32B:
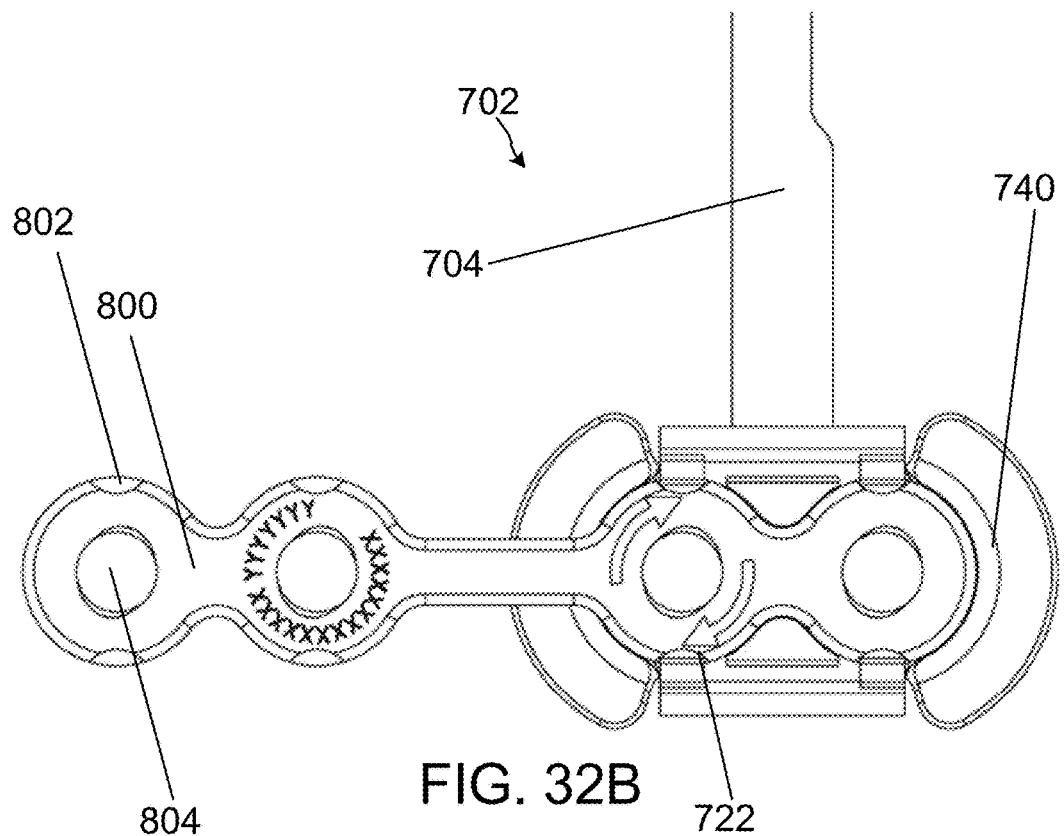

As shown in FIG. 32B, the plate 800 may include feet indentations 802. The feet indentations 802 may be disposed adjacent to a plate aperture 804. The feet indentations 802 may correspond to and receive a pair of coupling feet 722 disposed adjacent to a fastener aperture 712 to couple to and limit movement of a fastener guide 700 once coupled to the plate 800.

Figure 33:
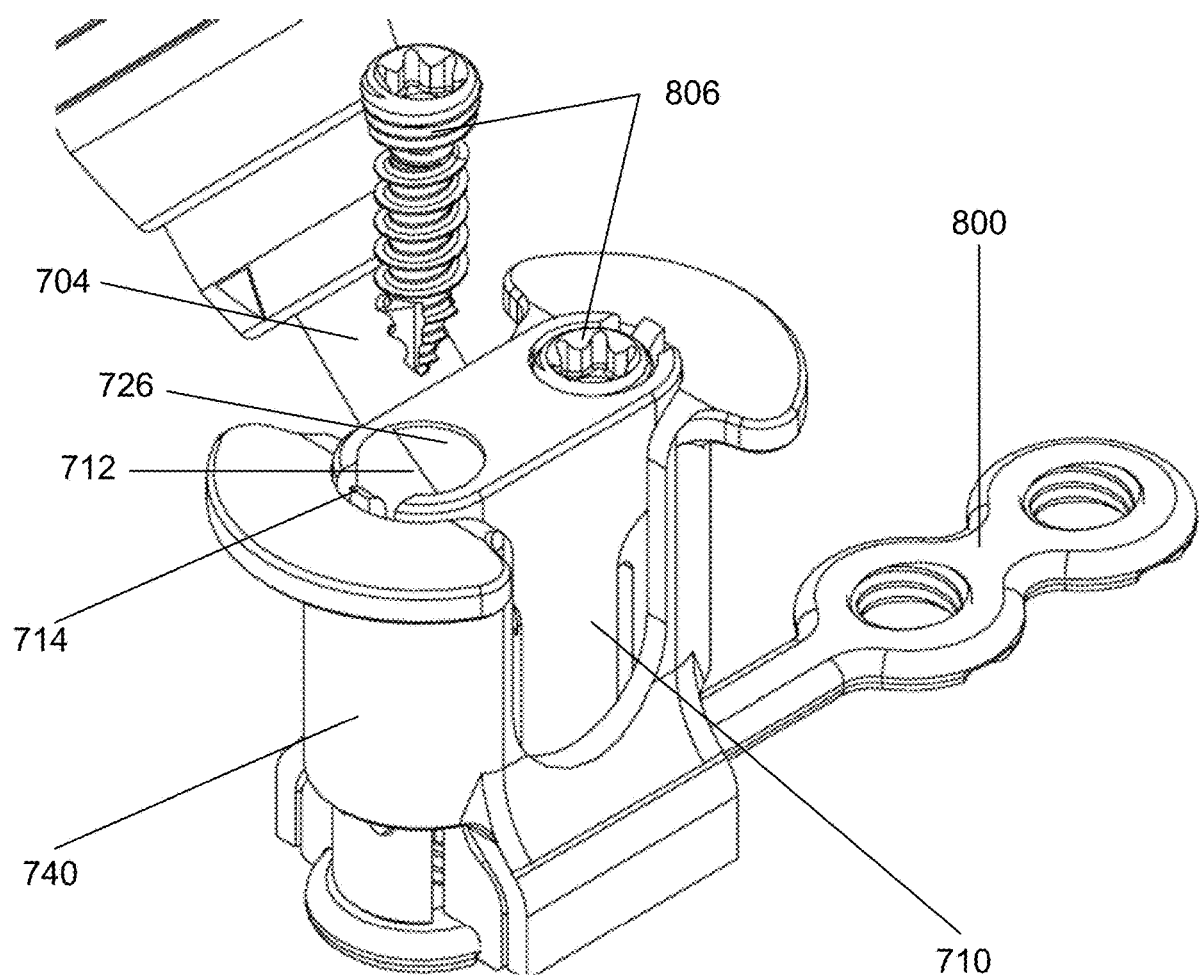
FIG. 33 illustrates a perspective view of the implant positioning device of FIG. 26 aligned with a plate and the collar, and receiving a fastener in accordance with an embodiment of the disclosure.

FIG. 33 illustrates the fastener guide portion 702 receiving fasteners 806 and the fastener guide portion 702 is aligned with a plate 800 in accordance with an embodiment of the disclosure. As described above, the fastener aperture 712 receives the fastener 806. The guide arm 714 may be used to releasably hold, guide, and position a fastener 806 that may be used to couple an orthopaedic fixation device, such as a plate, to a bone or other body part. Further, the slits 715 that may be disposed on opposite sides of the guide arm 714 allow the guide arm 714 to elastically move or flex away from the body 710 to allow the fastener 806 to be moved or pushed through the fastener aperture 712, when the fastener 806 is driven into a bone or other body part. An undercut 726 may also be provided within each fastener aperture 712. The undercut 726 is adapted to retain the fastener 806 and restrict the fastener 806 from being removed out the proximal end of the fastener guide portion 702. This assists in ensuring the fastener 806 does not inadvertently fall or shake out of the fastener guide portion 702 during use.

In one example, the fastener guide 700 may be preloaded with a fastener by placing the fastener in the first end of the fastener guide portion 702. This may include pushing the fastener into the fastener aperture 712 until a head of the fastener is gripped and held in place by the guide arm 714. The fastener guide 700 may also be coupled to a plate, such as plate 800, by pushing the coupling feet 722 onto the plate 800. This may cause the coupling feet 722 to move or flex away from each other and the body 710, and then snap back towards each other and the body 710 on the side of the plate 800 once pushed onto the plate 800. It should be appreciated that the implant fixation device 700 may be coupled to a plate, such as plate 800, prior to the insertion of the fastener.

It should be appreciated that one or more features of any of the fastener guides 100, 300, 500 and 700 may be removed, modified, or replaced with the features of any of the fastener guides 100, 300, 500 and 700. The fastener guides 100, 300, 500 and 700 may also be wholly or partially transparent to allow the user to view the progress of the fastener being inserted.

Although the devices, systems, and methods have been described and illustrated in connection with certain embodiments, many variations and modifications should be evident to those skilled in the art and may be made without departing from the spirit and scope of the disclosure. The disclosure is thus not to be limited to the precise details of methodology or construction set forth above as such variations and modification are intended to be included within the scope of the disclosure.

What is claimed is:

1. A fastener guide for an orthopaedic fixation device, comprising:
   a body;
   a collar disposed around the body;
   slits proximal to a first end of the body; and
   a guide arm formed by the slits proximal to the first end of the body and configured to directly contact and thereby to releasably hold a fastener in the fastener guide, each of the slits having a closed end and an open end opposite the closed end and being configured to allow the guide arm to elastically move to allow the fastener to be moved or pushed through the fastener guide, wherein the guide arm moves or flexes away from the body to allow the fastener to be received by the body.

2. The fastener guide of claim 1, wherein the guide arm includes two or more guide arms.

3. The fastener guide of claim 1, further comprising attachment arms formed at a second end of the body and configured to removably couple to a plate.

4. The fastener guide of claim 3, wherein the attachment arms include two or more attachment arms.

5. The fastener guide of claim 3, further comprising second slits proximal to the second end of the body forming the attachment arms.

6. The fastener guide of claim 1, wherein the body is tubular.

7. The fastener guide of claim 1, further comprising a ledge extending inwardly from a sidewall of the guide arms and configured to hold a head of the fastener.

8. The fastener guide of claim 1, wherein the guide arm moves away from the body to allow the fastener to be received by the body.

9. The fastener guide of claim 1, further comprising a fastener guide portion including the body, the slits, and the guide arm, wherein the body includes a first portion and a second portion, the slits include a first slit and a second slit, and in a circumferential direction of the fastener guide portion at the first end of the body the fastener guide portion includes the first portion of the body, the first slit, the guide arm, the second slit, and the second portion of the body.

10. A fastener guide for an orthopaedic fixation device, comprising:
    an extension portion having first and second ends, the first end is adapted to couple to a handle;
    a fastener guide portion coupled to the second end of the extension portion, the fastener guide portion including:
      a body;
      a fastener aperture in the body;
      a collar disposed around the body;
      slits formed proximal to a first end of the body; and
      a guide arm formed by the slits proximal to the first end of the body and configured to directly contact and thereby to releasably hold a fastener in the fastener aperture, each of the slits having a closed end and an open end opposite the closed end and being configured to allow the guide arm to elastically move to allow the fastener to be moved or pushed through the fastener guide, wherein the guide arm moves or flexes away from the body to allow the fastener to be received by the body.

\* \* \* \* \*